United States Patent
Hersam et al.

(10) Patent No.: US 7,414,250 B1
(45) Date of Patent: Aug. 19, 2008

(54) CRYOGENIC VARIABLE TEMPERATURE VACUUM SCANNING TUNNELING MICROSCOPE

(75) Inventors: Mark C. Hersam, Evanston, IL (US); Edward T. Foley, Chicago, IL (US)

(73) Assignee: Northwestern University, Evanston, IL (US)

( * ) Notice: Subject to any disclaimer, the term of this patent is extended or adjusted under 35 U.S.C. 154(b) by 135 days.

(21) Appl. No.: 11/291,210

(22) Filed: Nov. 30, 2005

Related U.S. Application Data

(60) Provisional application No. 60/632,368, filed on Nov. 30, 2004.

(51) Int. Cl.
  G01N 21/00 (2006.01)
  G01N 23/00 (2006.01)
  G21K 5/08 (2006.01)
  G21K 5/10 (2006.01)
  H01J 37/20 (2006.01)

(52) U.S. Cl. ............... 250/443.1; 250/306; 250/442.11; 250/441.11; 250/307; 250/310; 250/492.21; 73/105; 310/323.01; 310/323.02; 310/323.03; 977/871; 977/861; 977/854

(58) Field of Classification Search ................ 250/306, 250/443.1, 442.11, 441.11, 307, 309, 310, 250/492.21; 73/105; 310/323.01, 323.02, 310/323.03
See application file for complete search history.

(56) References Cited

U.S. PATENT DOCUMENTS

| | | | |
|---|---|---|---|
| 4,343,993 A | 8/1982 | Binning et al. | |
| 4,747,698 A | * 5/1988 | Wickramasinghe et al. | 374/6 |
| 4,841,148 A | 6/1989 | Lyding | |
| 5,198,667 A | 3/1993 | Glembocki et al. | |
| 5,276,672 A | 1/1994 | Miyazaki et al. | |
| 5,296,704 A | 3/1994 | Mishima et al. | |
| 5,589,686 A | 12/1996 | Ohara | |
| 5,654,546 A | * 8/1997 | Lindsay | 250/306 |
| RE37,203 E | 6/2001 | Elings et al. | |

OTHER PUBLICATIONS

Zhang, H., Memmert, U., Houbertz, R., Hartmann, U."A variable-temperature ultrahigh vacuum scanning tunneling microscope", Review of Scientific Instruments vol. 72 No. 6, pp. 2613 to 2617, 2001.*

Lyding, JW; Skala, S; Hubacek, JS; Brockenbrough, R; and Gammie, G; Variable-temperature scanning tunneling microscope: Rev. Sci. Instrum., Sep. 1988, 59 (9). 1897-1902.

Brockenbrough, RT; and Lyding, JW: Inertial tip translator for a scanning tunneling microscope; Rev. Sci. Instrum.; Aug. 1993, 64 (8), 2225-2228.

Foley, ET; Kam, AF; and Lyding, JW; Cryogenic variable temperature ultrahigh vacuum scanning tunneling microscope; Rev. Sci. Instrum., Sep. 2000, 71 (9), 3428-3435.

Kondo, Y; Foley, ET; Amakusa, T; Shibata, N; Chiba, S; Iwatsuki, M; and Tokumoto, H; Development of an ultrahigh vacuum scanning tunneling microscope cooled by superfluid $^4$He: Rev. Sci. Instrum., Jul. 2001, 72(7), 2977-2983.

(Continued)

*Primary Examiner*—Jack I. Berman
*Assistant Examiner*—Meenakshi S Sahu
(74) *Attorney, Agent, or Firm*—Reinhart Boerner Van Deuren s.c.

(57) ABSTRACT

A cryogenic variable temperature scanning tunneling microscope of novel design and component configuration, for use in conjunction with a variety of low temperature methodologies.

30 Claims, 18 Drawing Sheets

OTHER PUBLICATIONS

Stipe, BC; Rezaei, MA; and Ho; W; A variable-temperature scanning tunneling microscope capable of single-molecule vibrational spectroscopy: Rev. Sci. Instrum. Jan. 1999: 70 (1), 137-143.

Foley, ET; Yoder, NL; Guisinger, NP; and Hersam, MC; Cryogenic variable temperature ultrahigh vacuum scanning tunneling microscope for single molecule studies on silicon surfaces; Rev. Sci. Instrum., Dec. 2004, 75 (12), 5280-5287.

Guisinger, NP; Yoder NL; and Hersam, MC; Probing charge transport at the single-molecule level on silicon by using cryogenic ultra-high vacuum scanning tunneling microscopy, Proceedings of the National Academy of Sciences, Jun. 2005, 102 (25), 8838-8843.

Bedrossian. P; Scanning Tunneling Microscopy: Opening a New Era of Materials Engineering: Science & Technology Review, Aug. 1995, 4-11.

Ultra-High Vacuum, A Silicon-Based State Quantum Computer, University of California Los Alamos National Laboratory, http://www.lanl.gov/mst/SPML/ssqc.html, (last visited Oct. 25, 2006), 1-3.

Zetti Research Group, Research Project; Low Temperature, High Magnetic Field, Ultra High Vacuum Scanning Tunneling Microscope; http://www.physics.berkeley.edu/research/zettl/projects/stm.html. (last visited Oct. 25, 2006). 1-5.

* cited by examiner

Figure 4A                           Figure 4B

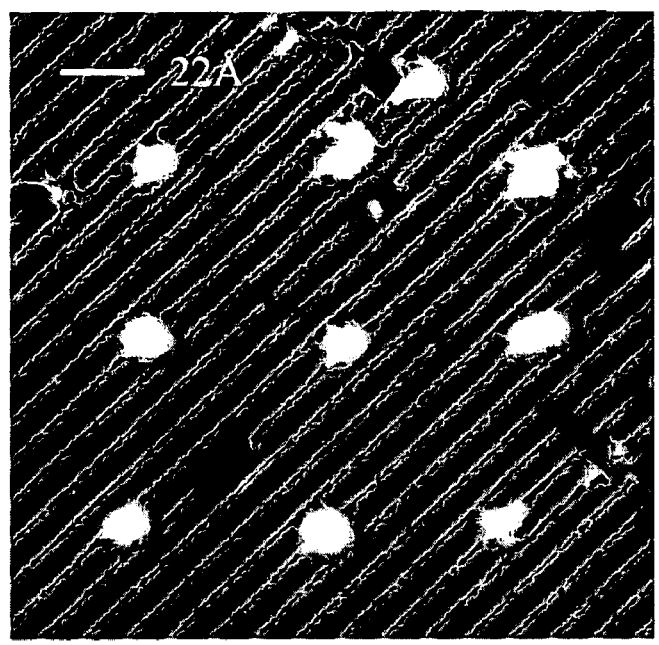
Figure 16
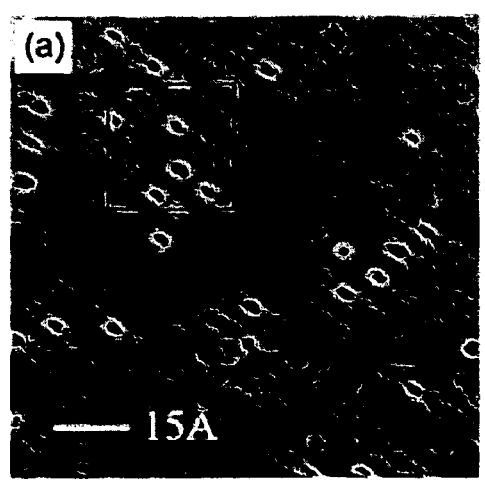 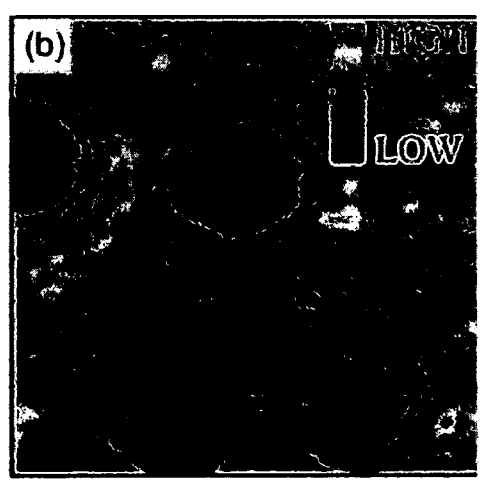
Figure 17A                Figure 17B

CRYOGENIC VARIABLE TEMPERATURE VACUUM SCANNING TUNNELING MICROSCOPE

This application claims priority benefit from application Ser. No. 60/632,368 filed Nov. 30, 2004, the entirety of which is incorporated herein by reference.

The United States government has certain rights to this invention pursuant to Grant No. DAAD 19-01-1-0521 from the United States Army Research Office to Northwestern University.

BACKGROUND OF THE INVENTION

Over the past 20 years, the ultrahigh vacuum (UHV) scanning tunneling microscope (STM) has established itself as an invaluable tool for studying the morphology and electronic structure of surfaces at the atomic scale. During this time, the minimum lateral feature size of silicon-based microelectronics has reached 90 nm and will soon make a transition to 65 nm technology. In this context, the STM has been used to develop a new understanding of silicon surfaces and to study the adsorption and desorption of individual atoms and molecules from silicon surfaces. For example, the study of STM-induced hydrogen and deuterium desorption from Si(100) surfaces has directly impacted the performance and reliability of microelectronics technology. Using a monolayer of hydrogen as a chemical resist, the STM has also been used to pattern and study molecular adsorption on the Si(100) surface. Furthermore, through feedback-controlled lithography (FCL), individual molecules have been patterned on silicon surfaces with atomic resolution. The study of individual molecules adsorbed onto the silicon surface, both isolated and adsorbed at controlled distances from one another, may enable the development of complementary molecular-scale electronic technologies that can be integrated with conventional microelectronic circuits.

When studying the adsorption of individual molecules on surfaces, a cryogenic variable temperature UHV STM offers a wider and more controlled experimental phase space than a room temperature UHV STM. In particular, at cryogenic temperatures, surface diffusion of physisorbed species may be controlled or eliminated, and thermal drift can be significantly attenuated. Much previous work of UHV STM manipulation and scanning tunneling spectroscopy (STS) of individual atoms and molecules has focused on metal surfaces at cryogenic temperatures. In these cases, the cryogenic UHV STM was used to manipulate individual physisorbed species that would be highly mobile at elevated temperatures, thus enabling the STM to make and break individual chemical bonds in a more controlled way. Furthermore, by reducing thermal broadening of the probing electronic energy distribution, spectroscopic resolution is improved at cryogenic temperatures. Through STS and inelastic electron tunneling spectroscopy, the cryogenic UHV STM has been used as a tool for the chemical identification of individual adsorbed molecular species and for obtaining the intra-molecular electronic structure of both randomly adsorbed molecules and patterned molecular arrays.

A variety of cryogenic variable temperature UHV STM designs have been presented in the literature. A common design problem centers on a trade-off between adequate coupling to the cryogen to maintain a stable low temperature while being sufficiently decoupled from any source of environmental vibrations. In many designs, the STM is clamped directly to a cryostat, and the cryostat and STM are vibrationally isolated. In other active cooling designs, a flexible thermal link exists between the STM and cryostat. In passive cooling schemes, the STM stage is located inside an isothermal enclosure, is then clamped to the cryostat for cooling, and is subsequently unclamped to perform STM.

SUMMARY OF THE INVENTION

In light of the foregoing, it is an object of the present invention to provide a cryogenic variable temperature scanning tunneling microscope apparatus and/or method(s) for use therewith, thereby overcoming various deficiencies and shortcomings of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to providing a scanning tunneling microscope apparatus designed and/or configured to resolve instability issues common to the prior art.

It is another object of the present invention to provide such an apparatus with continuous flow cryostat cooling, in combination with a concentric piezotube scanner, as can further be used in combination with designs of the type described herein for various component heat sinking and/or electrical isolation.

It can be another object of the present invention to provide one or more apparatus components of material choice heretofore unrecognized in the art, thereby providing improved apparatus performance and capabilities.

Other objects, features, benefits and advantages of the present invention will be apparent from this summary and the following descriptions of certain embodiments, and will be readily apparent to those skilled in the art having knowledge of various scanning tunneling microscope apparatus and related techniques. Such objects, features, benefits and advantages will be apparent from the above as taken into conjunction with the accompanying examples, data, figures and all reasonable inferences to be drawn therefrom, alone or with consideration of the references incorporated herein.

The present invention relates to a variable temperature ultrahigh vacuum (UHV) scanning tunneling microscope (STM) apparatus, components thereof and/or methods associated therewith. Without limitation, novel features and/or components of such an apparatus include continuous flow cryostat cooling combined with a concentric piezotube STM scanner. In addition, such an apparatus can comprise novel component designs and configurations for heat-sinking instrumentation feedthroughs and electrically isolated coaxial connectors. As discussed more fully below, such components and related configurations can be, at least in part, implemented through choice of material(s) affording unique performance properties under operating conditions. Component and apparatus performance can meet or exceed previous reports in all critical figures of merit. Without limitation, the wide range of tip and sample course translation (>1 mm) at low temperature is noteworthy. Considered alone or in combination with other component factors, such performance translates into a system of enhanced reliability and ease of use, as compared to the prior art.

Accordingly, the present invention can relate to a cryogenic variable temperature scanning tunneling microscope apparatus of the sort described herein. Such an apparatus can comprise a scanning tunneling microscope stage component and a cooling system. The cooling system can comprise a plurality of interposed compartments, one compartment between the periphery of another compartment, and the stage component can comprise a scanning tunneling microscope scanner, with the stage component positioned within one of the compartments. In certain embodiments, the cooling system can comprise an inner compartment and an outer compartment, with the stage component adjustably suspended from the inner compartment. Vibrational isolation can be achieved through the use of a plurality of suspension springs. In such embodiments, the stage component can be coupled to each of the suspension springs with an electrically-insulating mounting component. The springs can be compressed so as to position the stage component within the compartment.

Regardless of any stage/compartment configuration, the microscope scanner can comprise a sample holder component comprising two or more sample holder rails, each rail having at least in part a substantially rounded cross-sectional configuration. In certain embodiments, the rails can comprise titanium nitride; in certain other embodiments, each rail can comprise beryllium copper with a titanium nitride film or coating thereon or coupled thereto. In certain other embodiments, such rails can be electrically isolated from and/or heat-sunk to the sample holder component with a spacer component affording such properties, such spacer component comprising a material composition of the type described elsewhere herein. Likewise, each of the aforementioned compartments can comprise one or more apertures for connector and instrumentation feedthroughs, such apertures as can also be configured with a material component providing electrical isolation and/or heat-sinking properties.

In part, the present invention can also be directed to such an apparatus comprising a cooling system and a stage component of the sort described above, within a vacuum chamber component. As described elsewhere herein, such a chamber component can comprise a plurality of viewports and apertures for sample and/or instrumentation manipulation. Regardless, various embodiments of this invention can comprise a mirror configured with the stage and/or scanner components, for visual access to a scanner tip-sample interface. As can be contrasted with the prior art, such embodiments can provide, for the first time, direct observation of lateral translation of a probe stage at low temperature.

In part, the present invention can also relate to a method for quantatitive estimation of a molecular orbital energy of a single molecule and/or the use of an apparatus of this invention to achieve such an effect. Such a method can comprise providing a substrate degenerately p-type doped with a molecular component as a sample in a cryogenic scanning tunneling microscope apparatus comprising a piezoelectric scanner tip; applying a positive bias across the sample to induce an increase in conduction; and obtaining one or more of current-voltage measurements as a function of distance between the tip and the molecule component. Such measurements can be obtained at a temperature sufficient to maintain a substantially constant tip-sample distance over the course of measurements, and the bias can be sufficient to induce resonance with the highest occupied molecule orbital of the molecular component. In certain embodiments, the substrate can comprise an electrically-insulating material such as but not limited to silicon. Regardless of substrate identity, the molecular component can comprise a cyclopentene moiety. Without limitation, various other molecular components can be used in conjunction with such a method, as would be understood by those skilled in the art made aware of this invention. As such, molecular components can include, without limitation, those components comprising pi-systems and/or pi-systems pendent to an unsaturated moiety. Regardless, in certain embodiments, method temperature can be about 80 K, while in certain other embodiments, the temperature can be less than about 80 K.

In certain embodiments, an STM apparatus/system of this invention can operate from about 8.2 to about 300 K in a UHV environment with a base pressure of less about than $6 \times 10^{-11}$ Torr. Cooling can be achieved from about 300 to about 80 K within 3.5 h and from about 80 to about 8.2 K within 4.5 h. A base temperature of about 8.2 K can be maintained at a liquid helium consumption rate of 0.9 l/h. Such a design can allow for direct optical access to the tip-sample interface and direct line-of-sight dosing while the sample is mounted in the STM. The STM tip can be coarse translated laterally in two dimensions through an approximately 6-mm-diam area at all temperatures. With the feedback loop off, the drift in the tip-sample spacing is approximately 0.008 Å/min at about 8.2 K. Atomic resolution feedback controlled lithography can be performed on hydrogen passivated Si(100), and differential tunneling conductance maps can be gathered for isolated cyclopentene molecules on unpassivated Si(100), thus demonstrating that certain embodiments of this invention are well suited for studying single molecules—for example, on silicon surfaces from about 8.2 to about 300 K.

For instance, without limitation and as described below, Shapal-M® machinable aluminum nitride ceramic can be used with certain embodiments for heat-sinking electrical isolation. In yet another departure from the Lyding scanner of the prior art, beryllium copper can be used for the sample holder platform, which improves durability and allows for better heat sinking of the sample holder. Further, titanium nitride coated platform rails (available form Brycoat, Inc. of Safety Harbor, Fla.) can be used to improve the inertial translation of the sample holder at cryogenic temperatures. By varying the cryogen flow rate and actively heating the thermal shields, an STM of this invention can be operated at any temperature from 8.2 to 300 K. While at cryogenic temperatures, this invention allows for dosing of samples with an ex situ source through a variable leak valve or with an in situ evaporation/sublimation module. In addition, shuttered sapphire windows allow for direct optical access of the tip-sample junction at cryogenic temperatures. Such components, apparatus systems, and related methods can be used, non-exclusively, to perform atomic resolution FCL on hydrogen passivated Si(100) surfaces and to perform cryogenic STS studies of individual molecules on degenerately doped silicon surfaces at cryogenic temperatures.

BRIEF DESCRIPTION OF THE DRAWINGS

FIGS. 2D and 2E also show, schematically, various views of an STM piezoelectric scanner component.

FIG. 16. Constant current STM image of 3×3 grid of individual dangling bonds patterned with FCL at 300 K. The patterning conditions were 3.5 V sample bias and 2 nA tunneling current, while the imaging conditions were –2 V sample bias and 0.1 nA tunneling current.

FIGS. 17A-B. (A) Constant current STM image of individual cyclopentene molecules adsorbed to the clean Si(100)–2×1 surface at 80 K. The imaging conditions were –2.15 V sample bias and 0.1 nA tunneling current. (B) Differential tunneling conductance map of the area boxed in (A). The imaging conditions were –2.8 V sample bias and 0.1 nA tunneling current. Under these conditions, the isolated cyclopentene molecules appear as points of reduced differential tunneling conductance compared to the background silicon surface.

DETAILED DESCRIPTION OF CERTAIN EMBODIMENTS

Figures 1A, 1B:
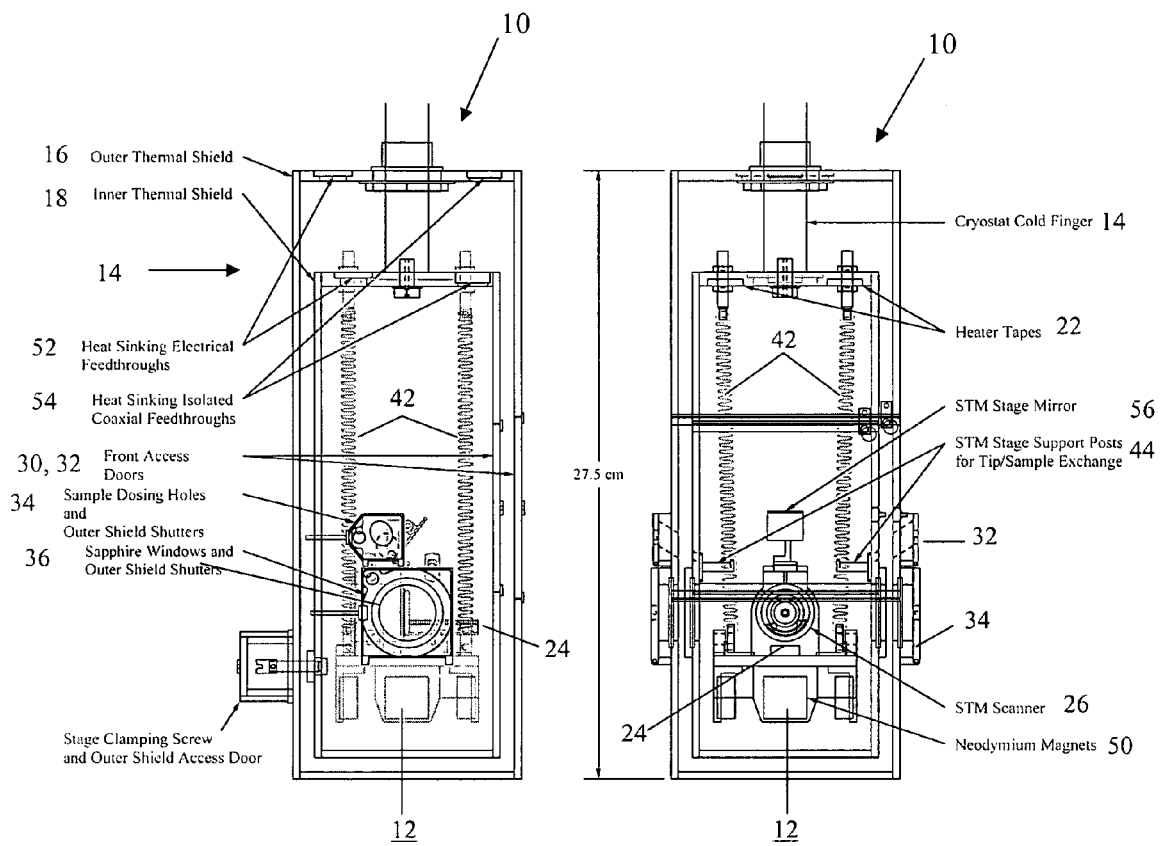
FIGS. 1A-B. Side view (A) and front view (B) of a STM stage and a cooling system, in accordance with certain aspects of an apparatus of this invention.
Figures 2A, 2B, 2C:
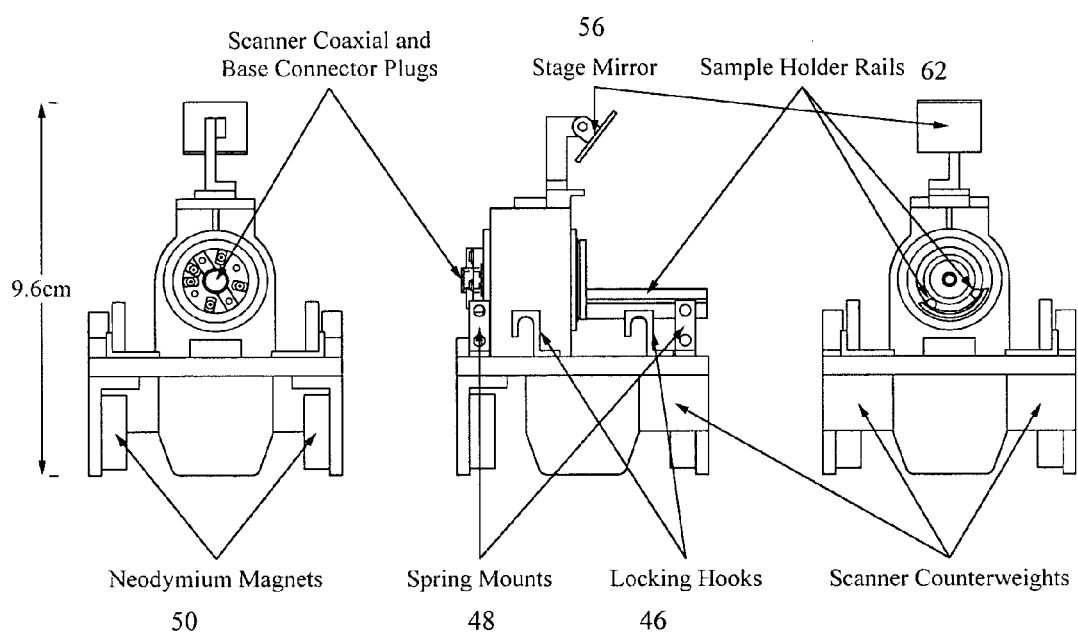
FIGS. 2A-E. Back view (A), side view (B), and front view (C) of an STM stage, showing magnet mounts, STM coaxial and base connector plugs, vibration isolation spring mounts, stage mirror, stage locking hooks, sample holder rails, and scanner counterweights.
Figure 2D:
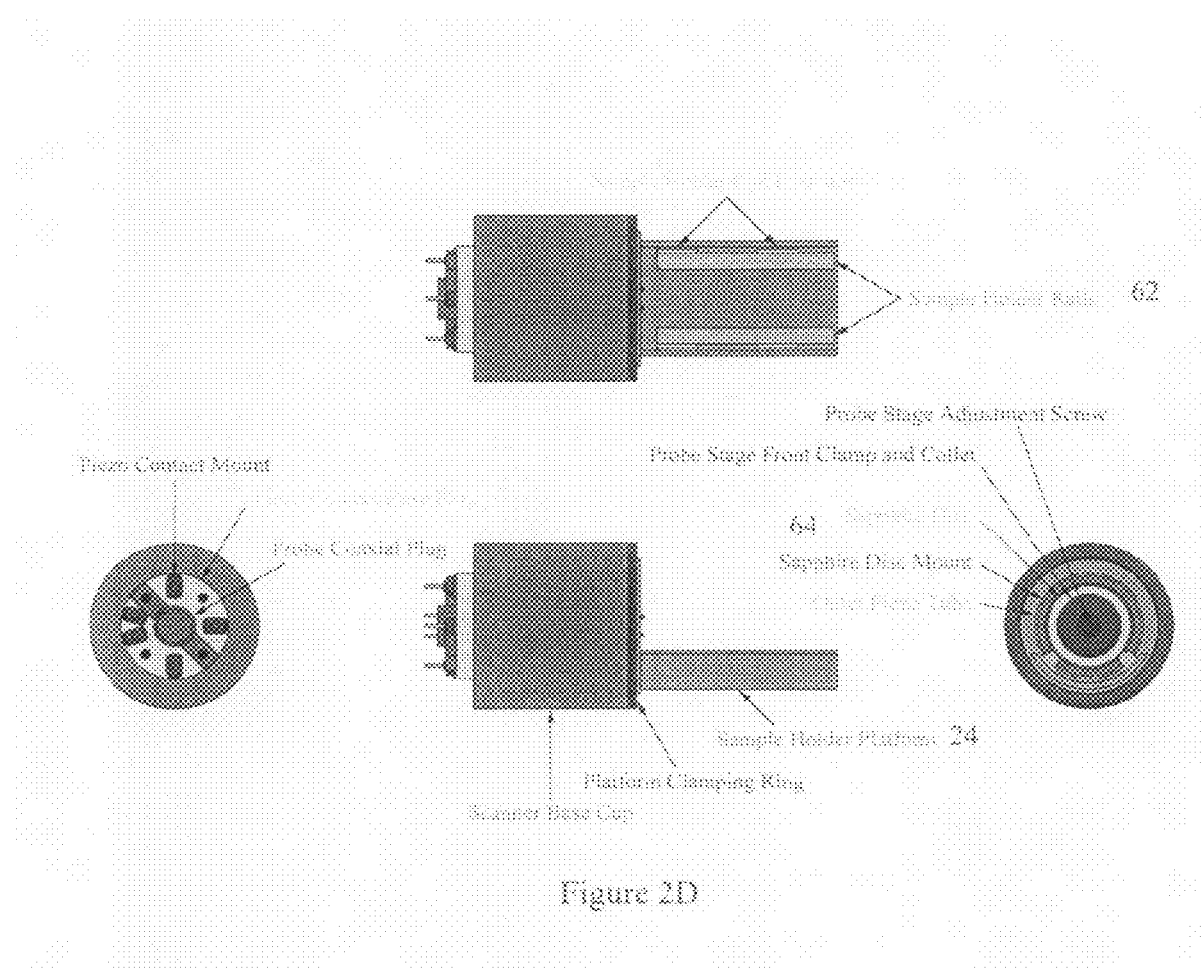

Schematics of an STM apparatus 10, comprising stage component 12, and cooling system 14 are shown in FIGS. 1A-1B. (Dimensional features in FIGS. 1A-B and several other figures are non-limiting, and provided only by way of reference with respect to certain embodiments.) Two thermal shield compartments 16 and 18 are mounted to the cold finger 20 of a continuous flow cryostat. (One such cryostat is the Helitran-3B Cryostat, available from Advanced Research Systems, Inc. of Allentown, Pa.) The STM stage 12 is suspended from the roof/wall of the inner shield 18. The transfer line for the cryostat has a vacuum jacket and an insulating helium gas return flow. Cryogen flow through the cold finger is regulated with a needle valve at the end of the transfer line inside the cryostat head and with flow meter valves on the cryostat head exhaust and the transfer line return. Variable temperature operation is achieved by adjusting the cryogen flow to an appropriate level and by using two heater components 22 mounted inside the roof of the inner thermal shield 18. A temperature controller (available from Lakeshore Crytoronics, Inc., of Westerville, Ohio.) and silicon diode temperature sensors are used for this purpose. Temperature sensors are mounted on the underside of the roof plate and on the outside bottom of the back panel of both thermal shields. (FIG. 3) In addition, temperature sensors are located on the STM stage component 12 and on the sample holder platform component 24 of the STM scanner 26. For cooling and warming the STM, the STM stage is clamped to the inner thermal shield with a clamping screw 28, which is mounted in the rear panel of the inner thermal shield. Once the desired temperature is attained, the stage is unclamped for performing STM. (See FIGS. 2 and 4)

Figure 6:
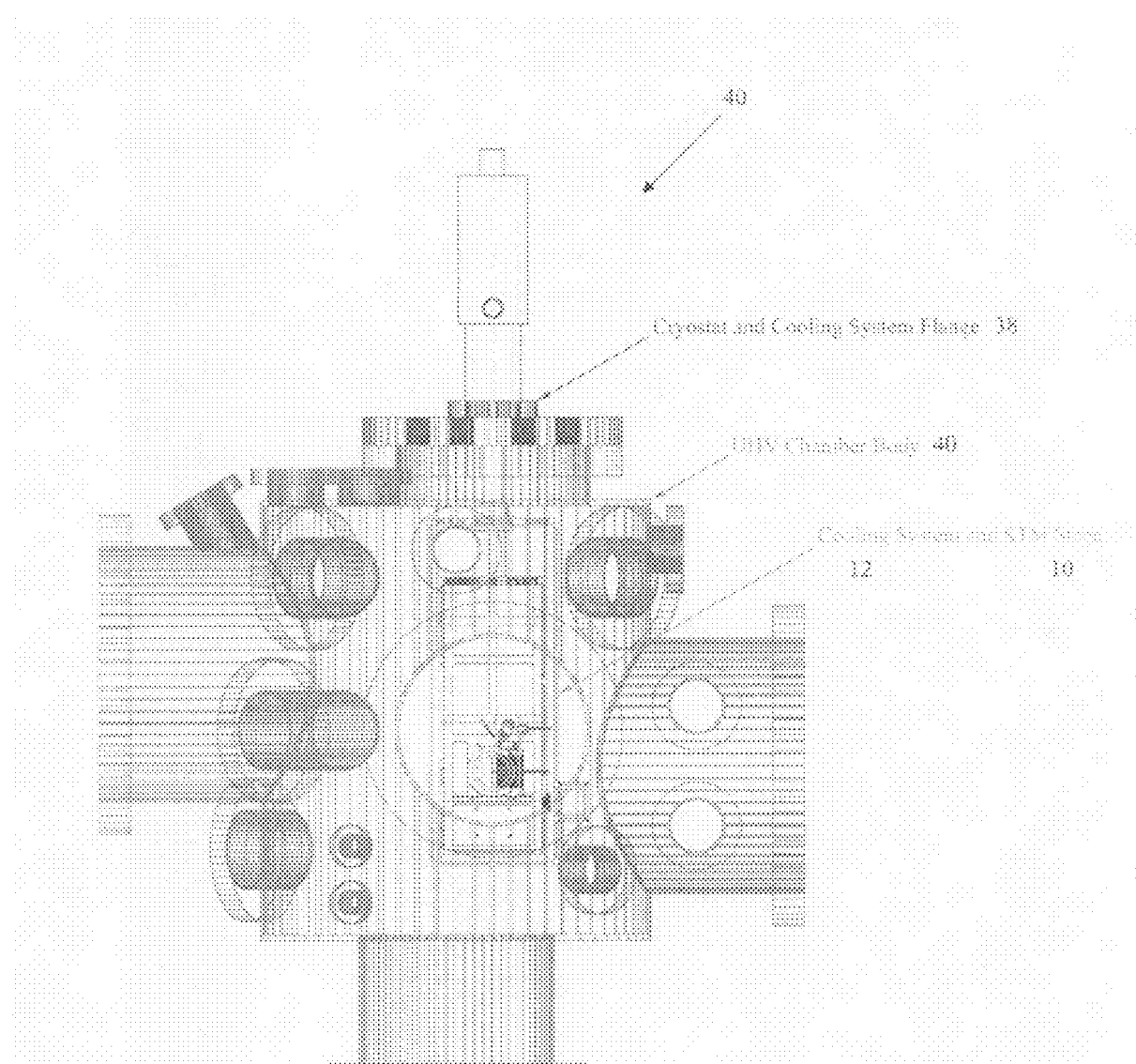
FIG. 6. A side view of an UHV chamber showing a cryostat and cooling system flange, and placement of the cooling system and STM stage within the UHV chamber.

Doors 30 and 32 are mounted on both thermal shields to allow for wobblestick access to the STM stage. A rear door on the outer thermal shield allows for rotary wobblestick access to the stage clamping screw. The rotary wobblestick also opens and closes the outer panel shutters for the dosing holes 34 and for the sapphire viewports 36 on either side of the thermal shields. All doors and shutters are magnetically latched using small nickel-plated neodymium magnets (e.g. ND38H neodymium iron boron, nickel plated, available from Dexter Magnetic technologies of Elk Grove Village, Ill.) and small 416 stainless steel disks. Almost all metal components of the thermal shields and STM stage are made from gold-over-nickel electroplated C101 OFHC copper or C17510 beryllium copper alloy to ensure good thermal conductivity and low emissivity of the entire assembly. Components of the thermal shields, such as the STM stage locking screw, stage support posts for tip/sample exchange, and hinge pins for the doors and shutters, are made from 6Al4V titanium. The entire cooling system and STM stage, including all electrical feedthroughs, are mounted onto a single 8 in. conflat flange 38 and weigh less than 13.5 kg. The compactness of the design allows for easy removal from the UHV chamber 40 for bench top maintenance. (See FIG. 6.)

The STM stage is suspended from the roof of the inner thermal shield by commercially available springs 42. Inconel 718 was chosen as the spring material to minimize changes in the spring constant from repeated thermal cycling to cryogenic temperatures and from UHV system bakeout. The STM stage may be raised to an elevated position, using the interaction of supports 44 and stage position components 46, for tip and sample exchange and to relax the stage springs during bakeout. (FIG. 4) These springs are electrically isolated from the STM stage by mounts 48 (Shapal-M® in preferred embodiments) and provide a stage resonant frequency of less than 1.4 Hz. Eddy current damping of the STM stage is achieved with four nickel-plated grade-38 neodymium magnets 50. Due to the symmetry of the magnet placement and the central position of the tip-sample gap on the STM stage, the strength of the magnetic field from the stage magnets at the position of the sample is less than 0.2 mT. (See FIGS. 2 and 4)

The STM tunneling current is shielded with UHV compatible low-triboelectric noise coaxial cable (e.g., available from Quirk Wire of West Brookfield, Mass.). With the STM tip out of tunneling range, the noise floor of the tunneling current preamplifier at $10^9$ V/A gain is less than 5 mV. Heat-sinking instrumentation feedthroughs 52 and electrically isolated coaxial connectors 54 are located on the roof of both thermal shields. (FIG. 3) Custom gold-over-nickel electroplated C17510 beryllium copper connectors, gold plated contact pins from machined pin solder-tail sockets (SPC Technology, Chicago, Ill.), Shapal-M®, Eutec-Rod® solder (Messer-Eutectic Corporation, Charlotte, N.C.), and Epo-Tek H74 and H21D epoxies (Epoxy Technology, Inc. Billerica, Mass.) are used in the construction of all electrical feedthroughs and connectors throughout the assembly. All wiring harnesses may be unplugged for easy removal, modification, or repair. Epoxies are used for mechanical bonding and heat sinking. All primary electrical connections are made with Eutec-Rod® solder or through gold-plated beryllium copper contacts. The wiring harness between the STM stage and the inner shield roof is made from polyimide coated copper wire (e.g. available from California Fine Wire of Grover Beach, Calif.). The coaxial cable between the STM stage and inner shield roof consists of a copper inner and outer conductor. The wiring harnesses between the two thermal shields and between the outer thermal shield and the 8 in. conflat flange are made from polyimide insulated phosphor bronze wire (e.g., from MWS Wire Industries, Westlake Village, Calif.), while the coaxial cables have copper inner conductors and stainless steel outer conductors. The wiring harnesses and coaxial cabling are placed inside fiberglass sheaths in a manner that preserves their flexibility. The sheaths are tied to the STM stage springs in two evenly spaced helical arcs in an effort to minimize vibrations conducted to the STM stage and to damp vibration of the stage springs. Heat-sinking electrical and coaxial connectors are mounted on the backside of the STM scanner, and the scanner is clamped to the STM stage in a way that allows for simple removal from the stage for maintenance.

Figure 2E:
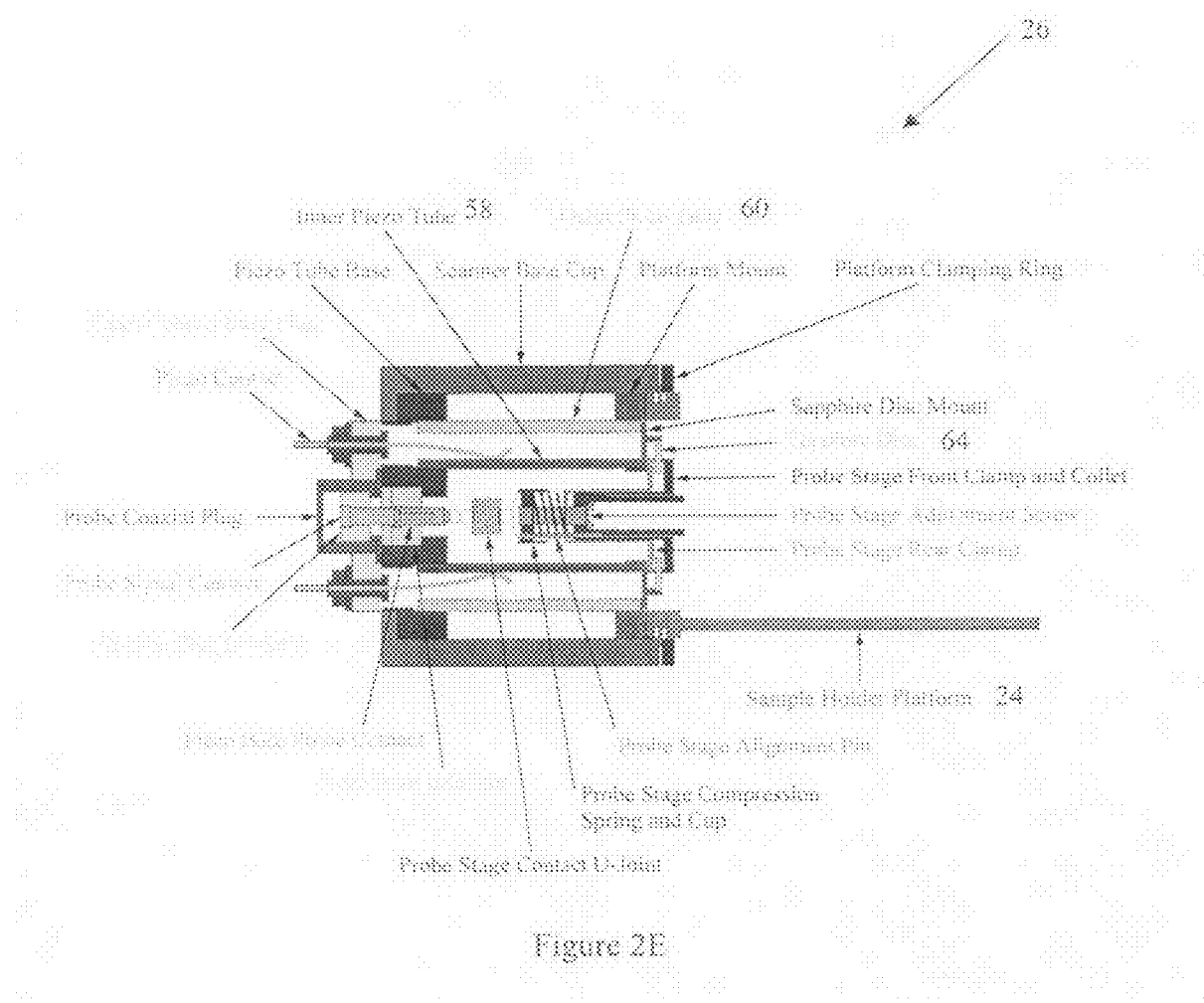
Figure 3:
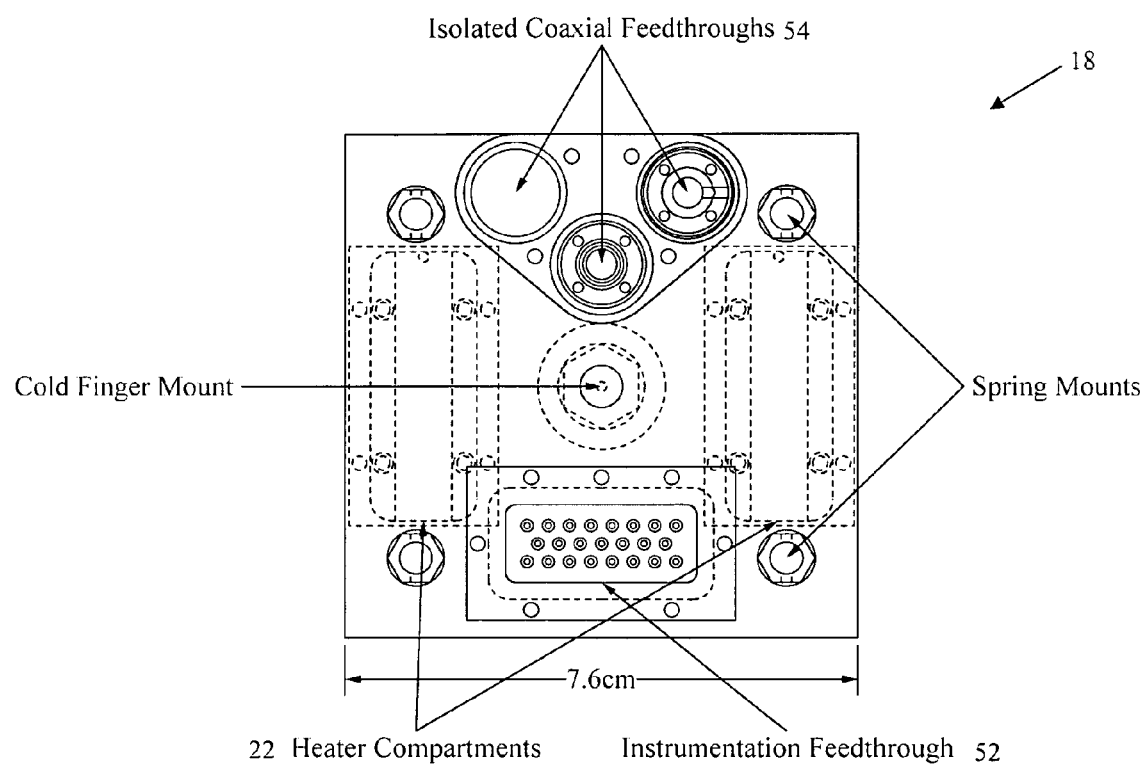
FIG. 3. Top view of the roof of an inner thermal shield compartment of a cooling system.
Figure 4:
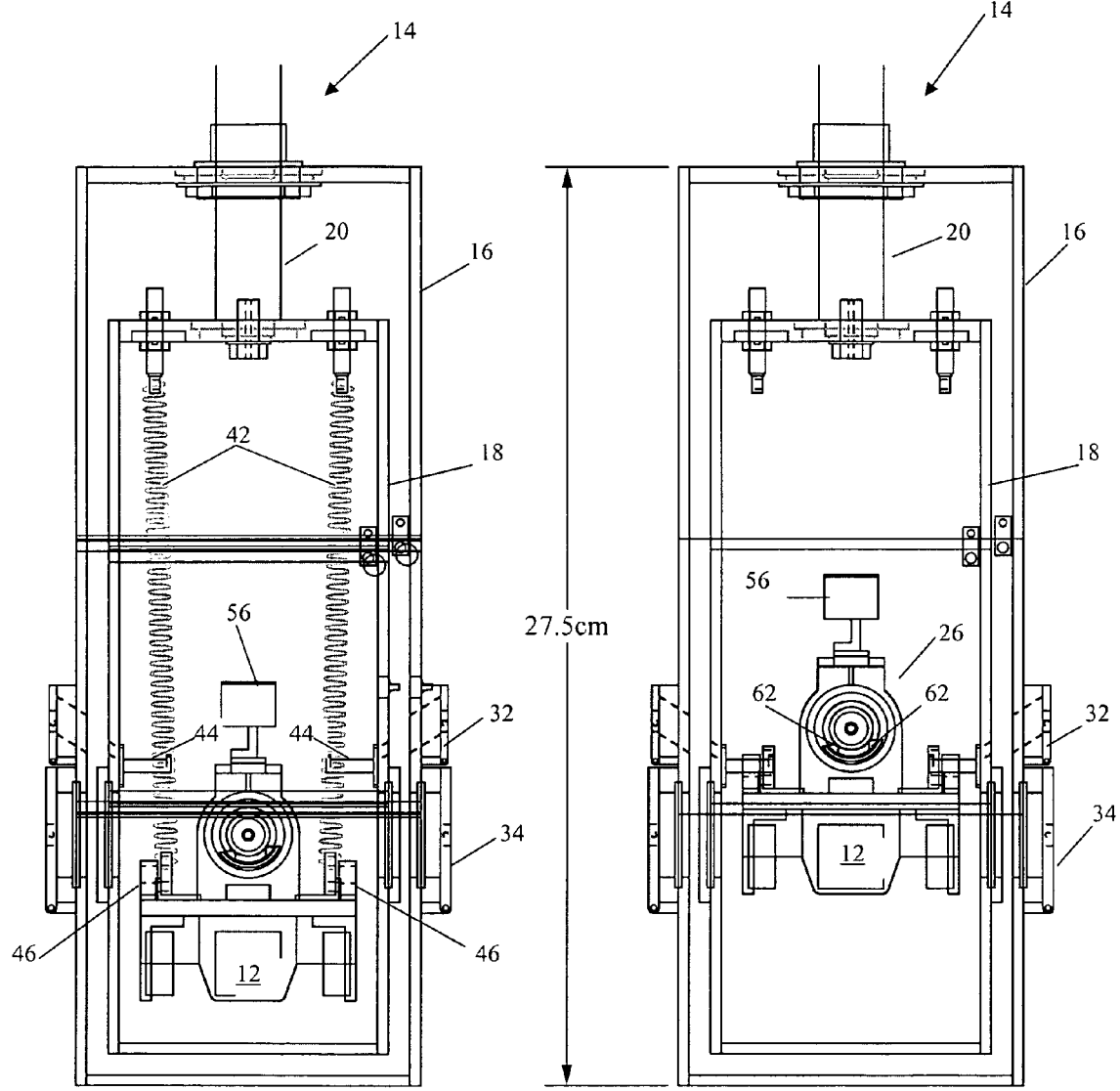
FIGS. 4A-B. Front views of an STM stage and cooling system showing the STM stage in the suspended position with the front doors closed (A) and in the locked position for tip and sample exchange (B). (Note that, in B, the doors of the thermal shields have been removed for clarity.)

A close-up view of the STM stage 12, with the front doors of the thermal shields open, is shown in FIG. 4. The STM is pictured in the upper position without a tip or sample present. Detail of the mount used to clamp the STM scanner 26 to the stage plate with its wobblestick handle and stage mirror 56 can be seen. An STM design of this invention utilizes two concentrically mounted piezotubes 58 and 60 (FIG. 2E). The sample holder platform 24 is mounted on the end of the outer piezotube 60. The sample holder is inertially translated on the titanium nitride coated beryllium copper rails 62 of this platform. (See, FIGS. 2 and 4) The feet of the sample holder, the sample holder platform rails, and the clamping surfaces of the tip stage have been highly polished with 0.05 μm alumina polishing cream. The tip stage is made from invar and is clamped to and can be inertially translated on a sapphire disk 64 mounted on the end of the inner scanning piezotube 58. The sapphire disk is metallized on its outer rim and soldered into an invar cup. This cup is then soldered onto the end of the inner piezotube. Eutec-Rod®, a tin/silver eutectic solder, is used to solder the sapphire disk into the invar cup. The tin/silver solder provides a strong joint between the sapphire disk and the invar cup that is robust to thermal cycling and can withstand the push and pull of tip exchange operations. Both piezotubes are soldered to the STM scanner components using Indalloy 290®, an indium/silver alloy solder (available from Indium Corporation of America, of Utica, N.Y.). The indium/silver solder allows for a strong, but compliant joint, which ensures the piezotubes are resistant to fracture from thermal cycling. Because an indium/silver alloy solder is used, UHV system bakeout temperatures in the vicinity of the STM stage are carefully monitored and kept below 120° C. With the stage suspended for scanning, the stage mirror provides for top-down visibility of the tip-sample gap during coarse translation of the tip stage and sample holder. The tip holders are made from 6AL4V titanium, while the sample holders have 6AL4V titanium sides and an electrically insulating Shapal-M® midsection. Molybdenum clips hold the silicon sample on the front side of the holder, and a molybdenum thermal shield located behind the sample minimizes radiative heating of the Shapal-M® midsection during sample preparation.

Regarding the UHV chamber 40, an 8 in. conflat cryostat and STM flange with its associated electrical feedthroughs are mounted into the top of the chamber. The UHV chamber and support frame/table assembly weighs approximately 800 kg and is floated on a Newport TBC/I-2000 pneumatic isolation system (from Newport Corporation of Irvine, Calif.). A 250 l/s turbo-molecular pump is used to pump a 41/2 in. conflat load lock, gas manifolds for surface passivation and sample dosing, and the UHV chamber during bakeout. The UHV chamber is pumped by a 640 l/s differential ion pump and by a titanium sublimation pump and cryoshroud assembly that can be isolated from the ion pump by a gate valve. Without cooling the cryostat, the base pressure of the UHV chamber is less than $6 \times 10^{-11}$ Torr. Gases can be introduced to the UHV chamber from the gas manifolds through variable leak valves. Tip preparation, sample preparation, and STM are all performed in this single UHV chamber system. Visual access is provided by 8 in. conflat viewports 66 on either side of the chamber and additional viewports on the front 10 in. conflat wobblestick flange and the rear 10 in. conflat rotary wobblestick flange. All chamber viewports are covered with aluminum foil when operating the STM at cryogenic temperatures. (See, FIGS. 5 and 6)

Figure 5:
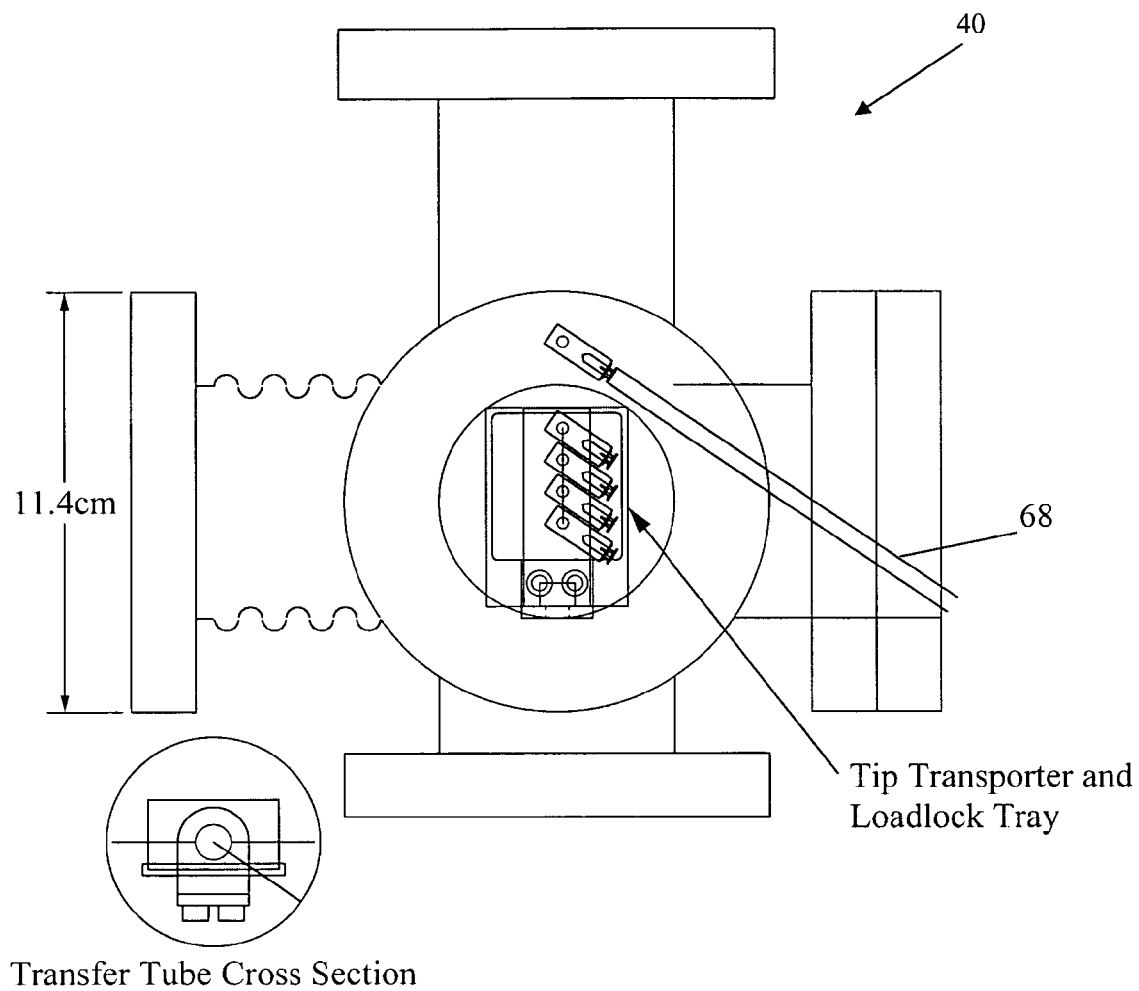
FIG. 5. Top schematic view of an UHV chamber loadlock showing a tip transporter and loadlock tray. A cross section of a loadlock tray in the transfer tube is also shown, inset.

A top view of a schematic UHV chamber is shown in FIG. 5. All tip, sample, and STM stage manipulations are performed with a wobblestick 68. The tip heating module, tips, samples, and sublimation modules are brought into the UHV chamber on a load lock tray. The tip heating module may be left in the UHV chamber, and tips can be transported in four collets located beneath the tray. Up to eight tips (using the tip heating module), four tips and two sample holders, or four tips and two sublimation modules may be brought into the chamber at one time. Garages are provided in situ for wobblesticks, tips, tip heating module, sample holders, and sublimation modules. On the left side of the outer thermal shield, a sublimation module heating station is aligned with a dosing hole in the thermal shields. On the right side of the outer thermal shield, a flexible dosing line is connected to an ex situ source via a variable leak valve and is similarly aligned with a dosing hole. (See, FIG. 6)

Figure 7A:
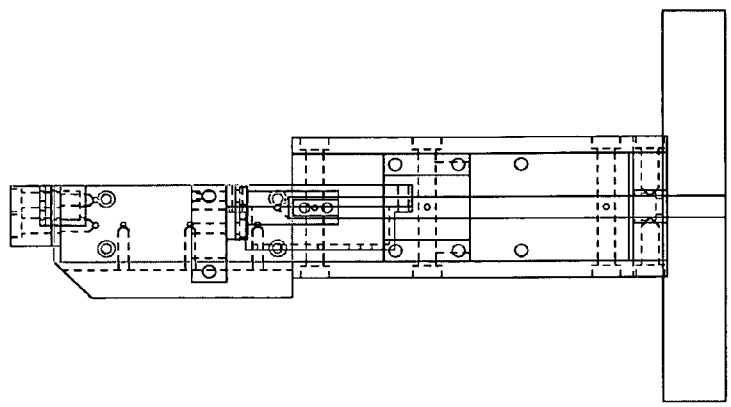
FIGS. 7A-C. Top view (A), and side views (B and C) of a tip and sample preparation station with the tip heating module (B) and sample holder (C) loaded showing the insulating platform and the degas filament enclosures.
Figure 7B:
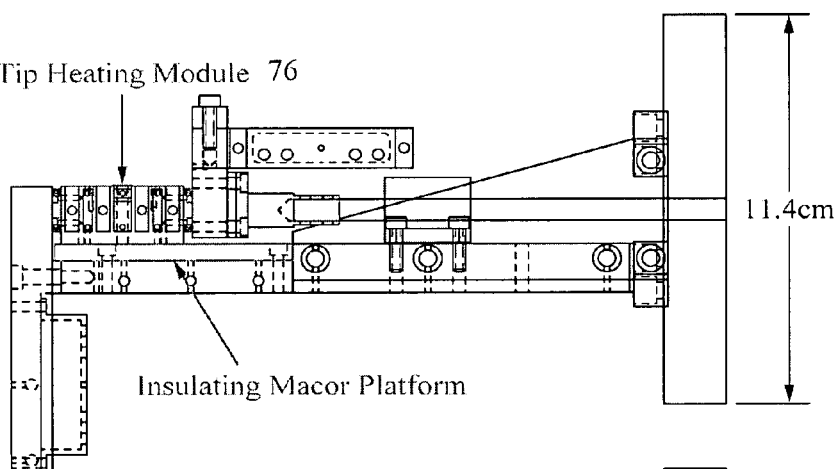
Figure 7C:
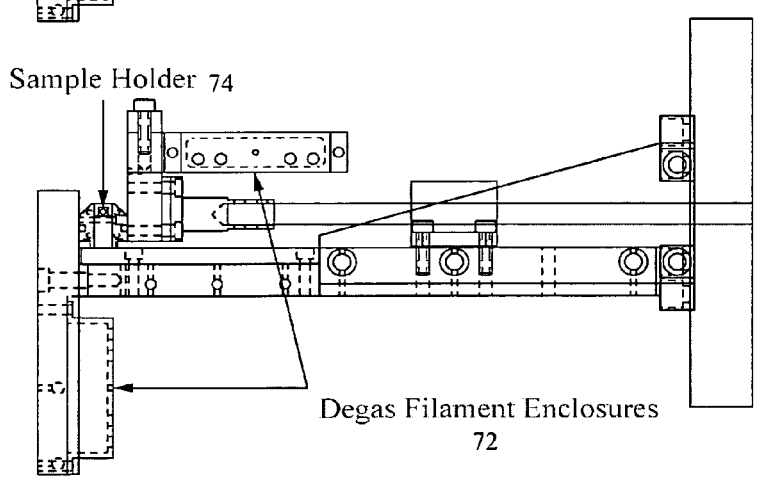

The tip and sample preparation station is located in front and to the right side of the outer thermal shield. The large copper conductors of this preparation station contain filament boxes 70 and 72, which aid in degassing operations. Sample holders or tip heating modules 74 and 76 are clamped between the conductors of the preparation station, where they are resistively heated. (See, FIG. 7) The two large conductors of the preparation station are each connected to 12-mm-diam copper conductor vacuum feedthrough posts with 12-mm-wide and 6-mm-thick flexible copper braid. The preparation station is conductively cooled using thermoelectric coolers connected to the feedthrough posts ex situ. On the far side of the preparation station, a filament is available for cracking gases during surface passivation. At the rear of the outer thermal shield is located a rotary wobblestick, wobblestick garage, and a door in the outer thermal shield leading to the stage clamping screw. Finally, handles for the shutters on the dosing holes and sapphire viewports are positioned on either side of the outer thermal shield.

To further demonstrate the utility and benefits of this invention, consider the study of charge transport through organic molecules covalently bound to silicon surfaces with room-temperature UHV STM. Experimental studies revealed doping-dependent unipolar negative differential resistance (NDR) in the current-voltage curves on individual molecules. The observation of NDR qualitatively agrees with a theoretical model proposed by Rakshit et al, which predicts that a semiconductor-molecule-vacuum-metal tunnel junction will behave as a molecular resonant tunneling diode. For degenerate p-type substrate doping, a positive sample bias will shift the energy of the valence band holes into resonance with the highest occupied molecular orbital (HOMO) of the molecule, thus leading to an increase in conduction. As the sample bias is further increased, the HOMO is shifted out of resonance and into the band gap of the semiconductor. This state of reduced conduction with increased bias is manifested as NDR in the current-voltage curve. The theoretical model relies on a fraction of the total applied bias being dropped across the molecule-semiconductor junction, so that the band edges of the semiconductor will experience energy shifts relative to the molecular orbitals. Furthermore, the model assumes that the molecular orbital energy levels are sufficiently close to the band edges of the semiconductor that they can be accessed by the experimentally applied biases. Although current data are consistent with these assumptions, additional experiments could verify the electrostatics and energetics of charge transport in silicon-based molecular electronic devices.

Experimental verification was made by taking a series of current-voltage measurements as a function of the distance between the STM tip and the organic molecule being probed. A variation in the tip-molecule spacing was expected to change the fraction of the total voltage that is dropped across the molecule-semiconductor junction, thus shifting the resonant tunneling condition in a systematic manner. In an effort to minimize experimental complications (e.g., sample contamination, thermal drift, and piezoelectric creep) that compromise measurements at room temperature, a cryogenic UHV STM was used at a temperature of 80 K. These cryogenic UHV STM measurements reveal that the resonant tunneling condition shifts to higher bias values for increasing tip-molecule spacing. When a capacitive equivalent circuit model is used, a quantitative fit is found for the experimental data, thus confirming the electro-statics initially proposed by Rakshit et al. Furthermore, from the fit, the equilibrium spacing of the HOMO energy with respect to the Fermi level of the substrate is estimated. These results imply that current-voltage measurements can be an effective means for performing chemical spectroscopy at the single-molecule level on degenerately doped silicon surfaces. In addition, such results suggest that the Rakshit model can be effectively used for the design of silicon-based molecular resonant tunneling devices.

Cyclopentene was chosen for this study because the adsorption process to the Si(100)–2×1 surface has been thoroughly studied in the literature and is well understood. The cyclopentene carbon-carbon double bond undergoes a cycloaddition reaction with a silicon dimer, thus orienting the molecule on the center of the dimer row. The molecules are expected to bind to the surface in a uniform and unique manner, which relieves the complexity of molecular systems that possess multiple binding configurations. A schematic representation of a cyclopentene molecule bound to a silicon dimer is shown in FIG. 8.

Performing STM charge-transport experiments on silicon at 80 K has several advantages over performing them at room temperature. When studying molecules adsorbed to the clean Si(100)–2×1 surface at room temperature, the surface typically becomes overwhelmed with spurious contamination within 24 h, thus limiting continuous experimental runtime. Furthermore, the presence of additional adsorbates can compromise the unambiguous identification of the intended molecule. Experiments are further complicated at room temperature by thermal drift of the sample or piezoelectric creep of the tip. This unwanted variability in the tip-sample spacing can compromise the definitive analysis of hysteresis in current-voltage measurements and introduces uncertainty into experiments where controlled variations in tip-sample spacing are required. On the other hand, because of effective cryopumping by the thermal shields at 80 K, the sample integrity is uncompromised for $\approx$10 days. Furthermore, thermal drift and piezoelectric creep are sufficiently low to perform multiple current-voltage measurements on the same molecule without detectable changes in the tip-sample spacing. The improved sample and microscope stability at 80 K thus simplify STM charge-transport measurements for organic molecules on silicon.

Current-voltage measurements were taken over individual cyclopentene molecules as a function of the tip-sample distance ($Z_{gap}$). The STM control software described herein allows for changes in the tip position ($\Delta Z$) relative to the initial tip-sample distance ($Z_0$) that is determined by the setpoint conditions of 0.1-nA tunneling current and –2-V sample bias. On the basis of the 10-Å value of the tip-sample spacing estimated from the current-voltage curve on the clean Si(100) surface, the measured 1-Å height of the cyclopentene molecule, and the known 5-Å actual height of cyclopentene, the value of $Z_0$ when the tip is positioned over a cyclopentene molecule is estimated to be $\approx$6 Å. Consequently, for variable tip-sample spacing measurements on cyclopentene, assume:

$$Z_{gap} = 6 \text{ Å} + \Delta Z. \qquad [1]$$

Figure 10:
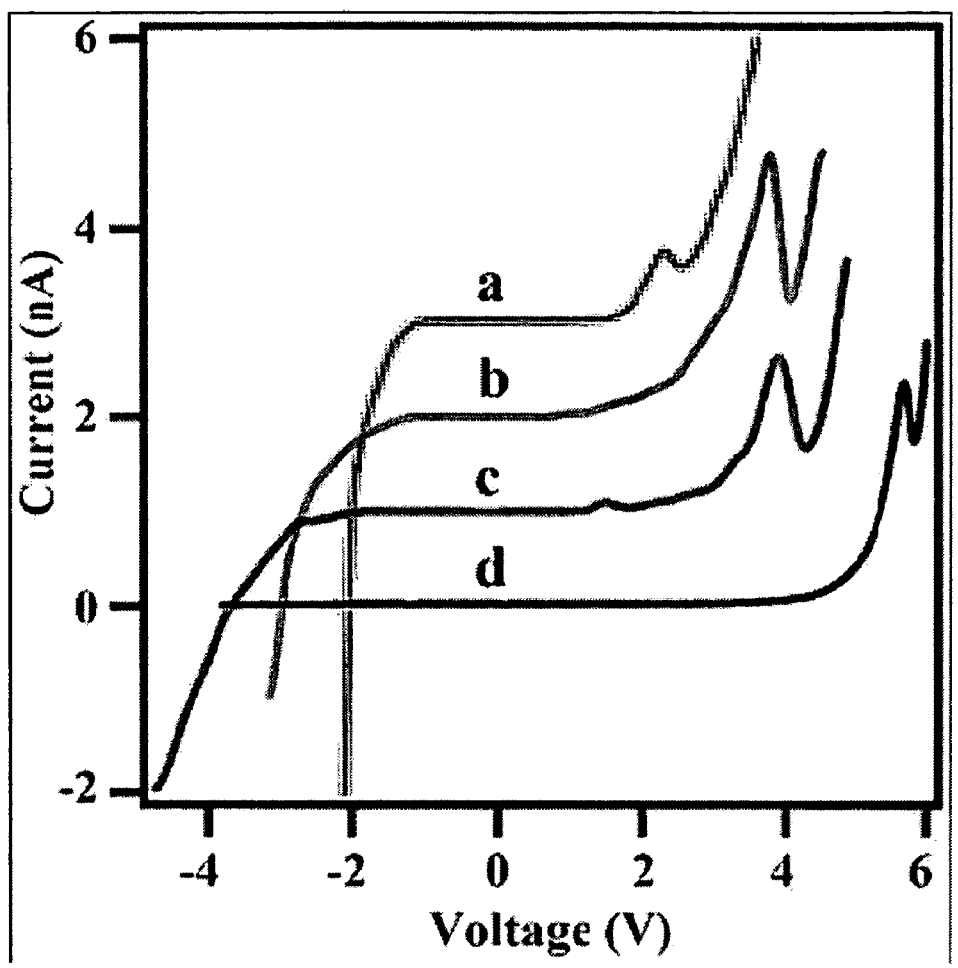
FIG. 10. A series of four different current-voltage curves taken over isolated cyclopentene molecules at different tip-sample distances. As the tip-molecule distance increases from curve a to curve d, the peak in the current-voltage curve shifts to higher voltage. Each of the curves is offset by 1 nA for clarity.
Figure 11:
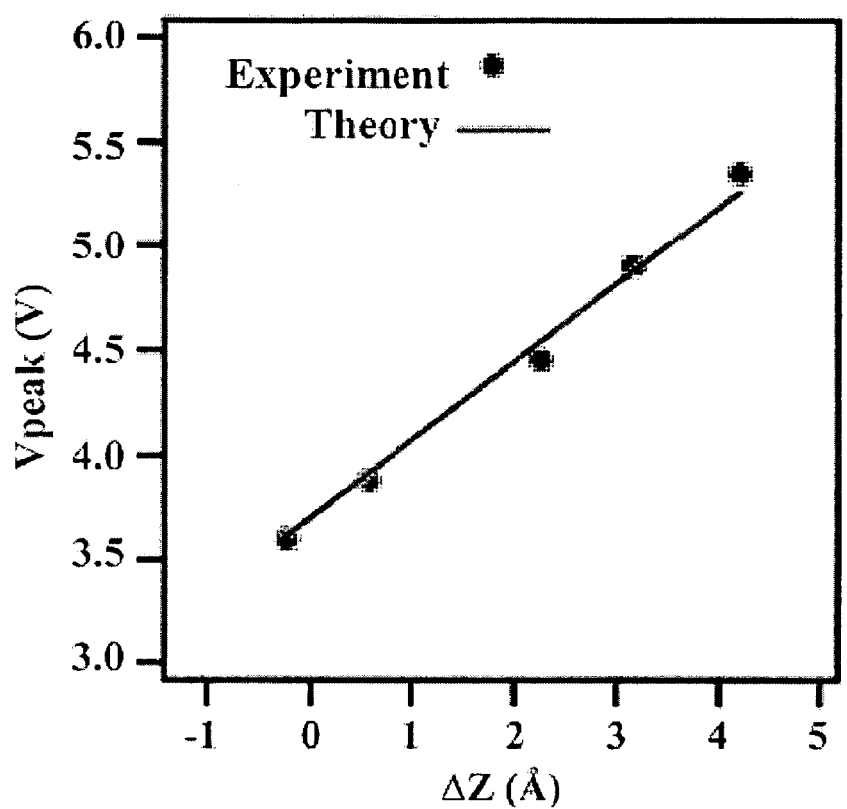
FIG. 11. An experimental and theoretical plot of the peak voltage ($V_{peak}$) versus the change in tip-sample spacing ($\Delta Z$). The theoretical curve fits the data reasonably well and allows for a quantitative estimate of the energy difference between the HOMO of the cyclopentene molecule and the Fermi level of the silicon substrate.

FIG. 9 shows four different current-voltage measurements taken at different values of $\Delta Z$ as specified by the STM control software. The current-voltage curves have been consecutively offset by 1 nA for clarity. From this figure, it is clear that $V_{peak}$ increases with increasing values of $\Delta Z$. It should be noted that the sharpness of the tip (as determined by the sharpness of the cyclopentene molecules in concurrent STM images) influences the peak-to-valley ratio of the observed NDR. For example, the tip appeared less sharp during imaging for curve a in FIG. 10 compared with the other measurements. Because a tip with reduced sharpness implies a broader spatial spread of the tunneling current, the measured current-voltage curve in this case would be a superposition of resonant tunneling through the molecule and direct tunneling to the surrounding clean silicon surface. Consequently, the peak-to-valley ratio is suppressed as experimentally observed. However, because this effect is not expected to influence the value of $V_{peak}$, variations in tip sharpness can be tolerated in these measurements. FIG. 11 is a plot of $V_{peak}$ versus $\Delta Z$ as determined from five current-voltage curves taken on individual cyclopentene molecules. Over this range of $\Delta Z$, the apparent linearity of this plot suggests that a simple model can be used to describe the electrostatics in a semiconductor-molecule-vacuum-metal tunnel junction.

In general, the electrostatic potential (V) can be calculated from the Poisson equation, $\nabla^2 V = \rho/\epsilon$, where $\epsilon$ is the dielectric constant and $\rho$ is the charge density, which must be determined self-consistently. In the limiting case where the density of states (DOS) is negligible, then the Poisson equation reduces to the Laplace equation: $\nabla^2 V = 0$. This case is commonly seen for electrically insulating materials and can be represented as a capacitive equivalent circuit. On the other hand, when the DOS is large, as would be the case for a metal, then the potential profile derived from the Poisson equation is better represented as a resistive equivalent circuit. The crossover from the capacitive limit to the resistive limit occurs when the quantum capacitance exceeds the electrostatic capacitance.

For a molecule, the DOS between the HOMO and the lowest unoccupied molecular orbital (LUMO) is negligibly small. Consequently, when the energy window between the electrochemical potentials of the two electrical contacts in a biased molecular junction exists in the HOMO-LUMO gap, the capacitive equivalent circuit model is a reasonable approximation. For a semiconductor-molecule-vacuum-metal tunnel junction, this description holds for low biases up to the resonant tunneling condition. Consequently, a capacitive equivalent circuit model will be used to determine the theoretical dependence of $V_{peak}$ on $\Delta Z$.

Figure 12:
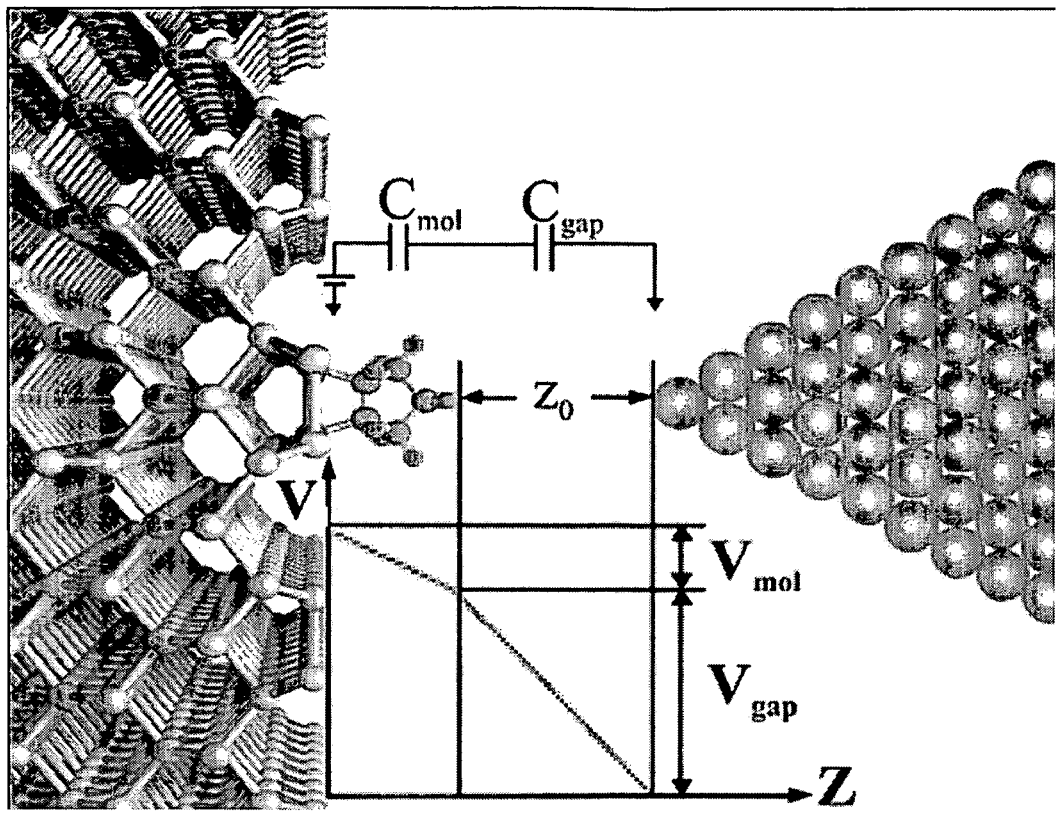
FIG. 12. Schematic illustration of the silicon-molecule-vacuum-tip tunnel junction and the capacitive equivalent circuit model, in accordance with use of the apparatus of this invention. During current-voltage measurements, the tip is grounded while the bias is applied to the sample. A qualitative plot of the voltage (V) versus tip-sample spacing (Z) has been inserted to illustrate the voltage drop across the molecule ($V_{mol}$) and the remaining voltage drop across the vacuum gap ($V_{gap}$). $Z_0$ is the setpoint distance between the tip and the molecule, which is established from the STM imaging conditions in constant-current mode (tunneling current=0.1 nA and sample bias=–2 V).

FIG. 12 schematically illustrates an isolated cyclopentene molecule bound to the Si(100)–2×1 surface that is being addressed with an idealized metal STM tip. As the simplest approximation, assume that the molecule and the vacuum gap can each be treated as one-dimensional parallel-plate capacitors. For further simplicity, the voltage drop due to band bending at the surface is also neglected. Under these assumptions, the electrostatic potential distribution is expected to follow the sketch in FIG. 12. Although such a model tends to simplify the underlying physics and chemistry, it leads to a quantitative fit of the data and thus provides insight into the electrostatics of semiconductor-molecule-vacuum-metal tunnel junctions.

Assuming one-dimensional parallel-plate capacitors, the capacitance of the molecule ($C_{mol}$) and the capacitance of the vacuum gap ($C_{gap}$) can be written in the following forms:

$$C_{mol} = \frac{\varepsilon_{mol}\varepsilon_0 A}{Z_{mol}} \quad [2]$$

and $$C_{gap} = \frac{\varepsilon_0 A}{Z_{gap}}, \quad [3]$$

where $\varepsilon_0$ is the permittivity of free space, $\varepsilon_{mol}$ is the relative permittivity of the molecule, $Z_{mol}$ is the height of the molecule, A is the cross-sectional area, and $Z_{gap}$ is the distance between the tip and molecule as defined previously in Eq. 1.

Assuming equal charge on each capacitor, the total voltage drop ($V_{tot}$) can be expressed in terms of the voltage drop across the molecule ($V_{mol}$) as $$V_{tot} = \frac{C_{mol}}{C_{tot}} V_{mol}, \quad [4]$$

where the total capacitance ($C_{tot}$) resulting from two capacitors in series is $$C_{tot} = \frac{C_{mol} C_{gap}}{C_{mol} + C_{gap}}. \quad [5]$$

Combining Eqs. 2-5 results in the following expression:

$$V_{tot} = \left(1 + \varepsilon_{mol} \frac{Z_{gap}}{Z_{mol}}\right) V_{mol}. \quad [6]$$

Figure 13:
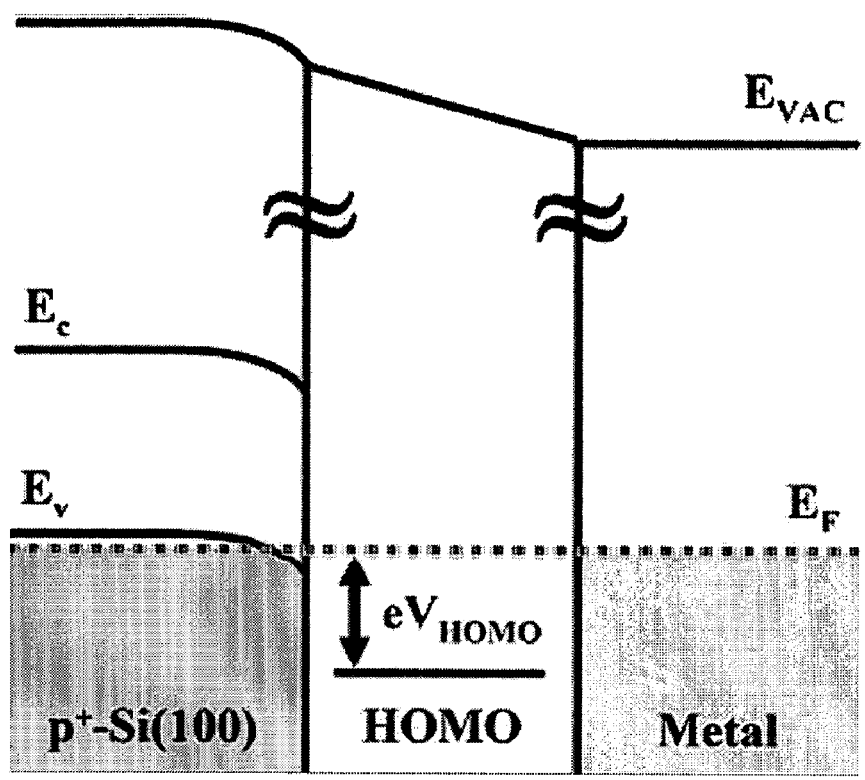
FIG. 13. An equilibrium energy band diagram of a semiconductor-moleculevacuum-metal tunnel junction for degenerately p-type doped silicon. The potential difference between the HOMO of the cyclopentene molecule and the Fermi level of the silicon substrate is labeled as $V_{HOMO}$. This parameter was quantitatively determined to be 0.74 V from the theoretical fit of FIG. 4. In this diagram, $E_C$ is the conduction band edge, $E_V$ is the valence band edge, $E_F$ is the Fermi level, and $E_{vac}$ is the vacuum energy level.

FIG. 13 is an equilibrium band diagram for this semiconductor-molecule-vacuum-metal tunnel junction. When the average voltage on the molecule ($V_{mol}/2$) matches the equilibrium potential difference ($V_{HOMO}$) between the HOMO level and the semiconductor Fermi level, the resonant tunneling condition will be achieved and thus the total voltage will be equal to $V_{peak}$. With this constraint, Eq. 6 can be rewritten in the following form:

$$V_{peak} = 2\left(1 + \varepsilon_{mol} \frac{Z_{gap}}{Z_{mol}}\right) V_{HOMO}. \quad [7]$$

The experimentally measured values of the height and relative permittivity of cyclopentene are 5 Å and 1.26, respectively). Applying these values and the expression for $Z_{gap}$ from Eq. 1 into Eq. 7 yields the following relationship between $V_{peak}$ (in units of volts) and $\Delta Z$ (in units of Å):

$$V_{peak} = (5.024 + 0.504\Delta Z) V_{HOMO}. \quad [8]$$

Eq. 8 was used to fit the experimental data. As seen in FIG. 11, the quality of the fit is reasonable, thus justifying the simplicity of the model over this range of $\Delta Z$. The fitting parameter of $V_{HOMO} = 0.74$ V provides an estimate of the alignment of the cyclopentene molecular orbital with the Fermi level of the substrate. Consequently, the systematic study of charge transport through a semiconductor-molecule-vacuum-metal tunnel junction as a function of tip-sample distance coupled with a capacitive equivalent circuit and resonant tunneling model provides a means for quantitatively estimating molecular orbital energies at the single-molecule level.

Such methods and related studies can be affected through use of apparatus of the sort described herein, operation of which would be understood by those skilled in the art of scanning tunneling microscopy. Such operation and function as are described in U.S. Pat. No. 4,343,993, the entirety of which is incorporated herein. Likewise, such artisans are aware of the availability of various computer/electronic systems useful in conjunction with the present invention, relating to scanner control, cryogen variation and the like. Without limitation, such systems are available through RHK, a manufacturer of such control systems. Likewise, without limitation, the preceding results will be understood by such artisans and can be at least in part attributable to one or more of the component designs and/or configurations described above. For example, use of beryllium copper sample holder and/or rail components enhance heat conduction to the holder component which rests, and is inertially translated, on top of the rails of the scanner platform. Such a design and/or material choice further enhances the reliability of the scanner component. Concentric tube designs of the prior art used quartz susceptible to fracture from thermal cycling and accidental breakage. The present invention can be used to reduce such issues and enhance overall performance and utility.

EXAMPLES OF THE INVENTION

The following non-limiting examples and data illustrate various aspects and features relating to the components, apparatus, systems and/or methods of the present invention, as are available through various embodiments thereof including but not limited to those described above. In comparison with the prior art, the present invention provides results and data which are surprising, unexpected and contrary thereto. While the utility of this invention can be illustrated through representative apparatus/system embodiments and components used therewith, it will be understood by those skilled in the art that comparable results are obtainable with various other components, apparatus, systems and related methods of use, as are commensurate with the scope of this invention.

Example 1

Figure 14A:
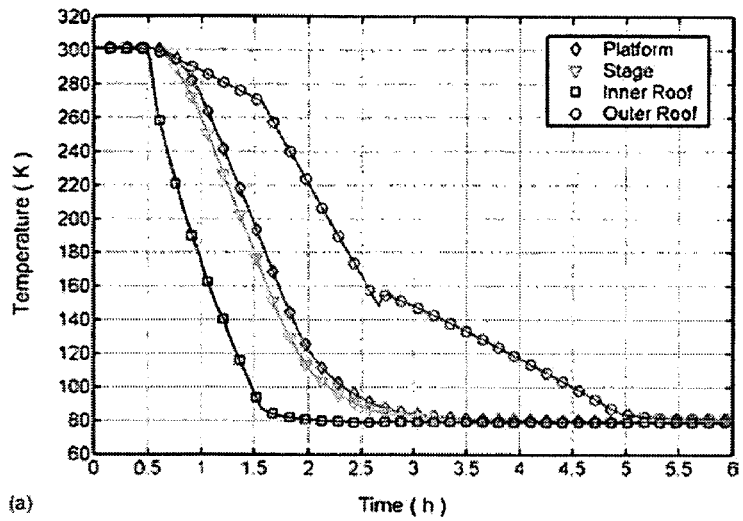
FIGS. 14A-B. Cooling performance from 300 to 80 K (A) and from 80 to 8.2 K (B).

The cooling system performance between 300 and 80 K is shown in FIG. 14A. After coarse translating the sample out of tunneling range, the STM stage is clamped to the front wall of the inner thermal shield. The cryostat transfer line is inserted into the liquid nitrogen Dewar, and 30 kPa of dry nitrogen gas back pressure is applied to the Dewar. The needle valve of the transfer line inside the cryostat head and flow meter valves on the cryostat head exhaust and transfer line return are set for maximum flow. In less than 30 min, the cryogen begins to cool the assembly. Since the roof of the inner thermal shield is directly connected to the end of the cold finger, this part of the assembly begins to cool first. Shortly thereafter, the STM stage plate and STM sample holder platform follow and eventually cool at the same rate as the inner roof. When the STM stage is cooling at a maximum rate of 2.3 K/min, the separation in temperature between the STM stage and sample holder platform can be as much as 15 K. When the temperature of the outer thermal shield reaches 150 K, final adjustments are made to minimize the cryogen flow necessary to bring the STM stage to 79.6 K. At this flow setting, the inner and outer thermal shields equilibrate to a temperature of 79.1 and 81.2 K, respectively. The STM stage is then unclamped from the inner thermal shield and scanning can commence. In total, STM can be performed at 80 K within 3.5 h of initial cryogen flow.

Example 2

Figure 14B:
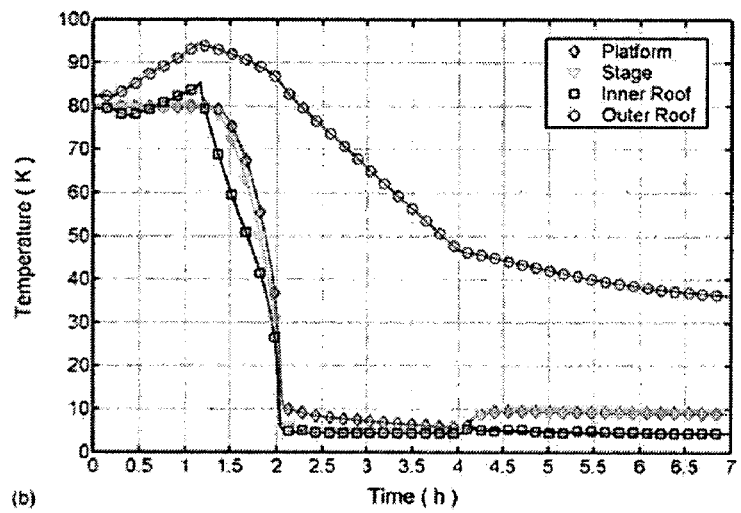

The cooling system performance between 80 and 8.2 K is shown in FIG. 14B. The pre-cooling liquid nitrogen flow is stopped by closing the flow meter valves on the cryostat head exhaust and transfer line return while relieving the back pressure on the liquid nitrogen Dewar. Before inserting the transfer line into the liquid helium Dewar, dry helium gas is flowed through the transfer line and cryostat head to ensure that any residual liquid nitrogen and nitrogen gas are flushed from the cryostat and transfer line. When the temperature of the inner roof climbs to 80 K, the transfer line is inserted into the liquid helium Dewar, and a back pressure of 30 kPa of dry helium gas is applied. The needle and flow meter valves of the cryostat are set for maximum flow. About 1 h after the changeover to liquid helium is initiated, the temperature of the inner and outer thermal shields, which have drifted up to about 85 and 95 K, respectively, begin to cool again. When the temperature of the inner roof falls below 80 K, the STM stage is locked, and the STM stage and sample holder platform begin tracking the temperature of the inner roof shortly thereafter. The STM stage cools at a maximum rate of 10 K/min below 20 K. The inner roof and STM stage equilibrate to 4.5 K. Below 10 K, the sample holder platform temperature falls more slowly than the STM stage. When the outer shield temperature falls below 50 K, the helium flow is adjusted to the minimum flow required to bring the STM stage and sample holder platform to a base temperature of 8.2 K. After this flow setting is achieved, the STM stage is unclamped from the inner shield, and the STM stage and sample holder platform temperatures rise and equilibrate at 8.2 K. This temperature rise is due to imperfect heat sinking of the wiring and cable harnesses leading to the STM stage and radiative heating due to imperfect sealing of the thermal shields to light. In steady state, the inner and outer thermal shields equilibrate to base temperatures of 4.5 and 37 K, respectively. Less than 5 l of liquid helium are consumed in cooling the STM from 80 to 8.2 K, and the base temperature of 8.2 K is maintained at a helium consumption of 0.9 l/h. In total, STM can be performed within 4.5 h of initiating the changeover from liquid nitrogen to liquid helium cooling.

Example 3

Through the use of beryllium copper for the sample holder platform and titanium nitride coated platform rails, durability in thermal cycling, thermal conductivity, and inertial translation of the sample holder at cryogenic temperatures have been improved. Thermal drift and resonant frequency characteristics are similar to that previously reported in the literature. At 8.2 K, the drift in tunneling current is less than 1.7%/min with the feedback loop disengaged. This percentage change in the tunneling current translates to a drift in tip-sample spacing of approximately 0.008 Å/min. To illustrate the insensitivity of the design to acoustic noise, it should be noted that these drift values remain unchanged even with a sustained background acoustic noise level in the laboratory up to 68 dB. The response of the piezotubes at 300 K (216 Å/V) decreases by a factor of 2.6 at 78 K (82 Å/V) and by a factor of 5.4 at 8.2 K (43 Å/V). In order to ensure adequate coarse translation of the tip stage and sample holder, ±220 V DSP-based control electronics have been constructed. This voltage range yields a maximum scan window of 9.5 µm×9.5 µm at 300 K and 1.9 µm×1.9 µm at 8.2 K. Through coarse translation of the tip stage, however, this scan window can be moved in two dimensions through a 6-mm-diam area at any temperature from 8.2 to 300 K.

Example 4

Figures 15A, 15B, 15C:
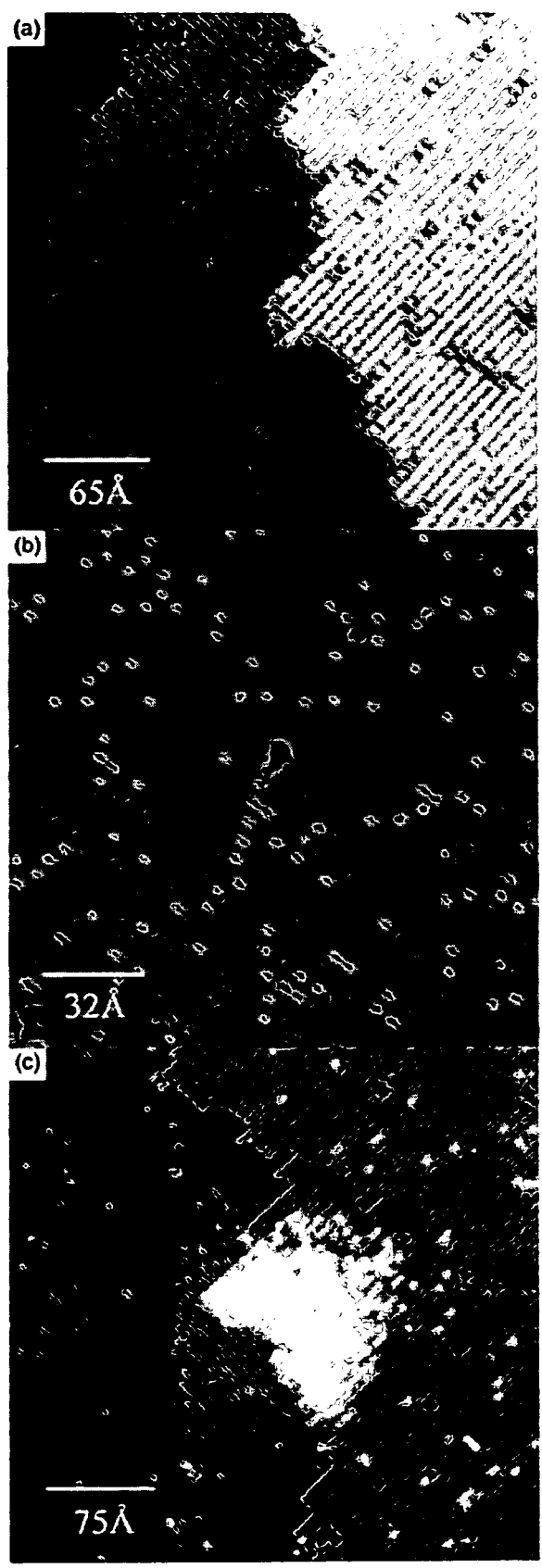
FIGS. 15A-C. (A) Constant current STM image of the clean Si(100)–2×1 surface at 30 K. The imaging conditions were –2 V sample bias and 0.1 nA tunneling current. (B) Constant current STM image of a submonolayer coverage of cyclopentene on the Si(100) surface at 80 K. The imaging conditions were –2 V sample bias and 0.1 nA tunneling current. (C) Constant current STM image of a depassivated square of clean silicon patterned on the Si(100)–2×1:H surface at 8.2 K. The patterning conditions were 4.5 V sample bias and 2 nA tunneling current, while the imaging conditions were –2 V sample bias and 0.1 nA tunneling current.

STM scanning performance is demonstrated in FIG. 15 at 300, 80, and 8.2 K. Tips are fabricated from tungsten wire electrochemically etched in NaOH. After introduction into UHV, tips are degassed above 600° C. for at least 6 h. Degenerately doped n-type (<0.005 Ωcm, both As and Sb doped) Si(100) samples are used (e.g., available from Virginia Semiconductors of Fredericksburg, Va.). The samples are cut to size (5 mm×10 mm) with a diamond scribe and ultrasonically cleaned in isopropyl alcohol before introduction into UHV. The samples are degassed at 650° C. for at least 6 h before being repeatedly flashed at 1250° C. to produce a clean surface. An image of the clean Si(100)–2×1 surface at 300 K is shown in FIG. 15A.

Example 5

After preparing the clean Si(100)–2×1 surface, molecules can be deposited onto the surface using the sublimation stage or the variable leak valve. To demonstrate this capability, the clean Si(100)–2×1 surface was exposed to $10^{-8}$ Torr of cyclopentene for 1 min, which results in a submonolayer coverage. FIG. 15B illustrates a STM image taken at 80 K of the resulting surface. The apparent conformation of the cyclopentene molecules on the Si(100)–2×1 surface agrees with previous reports.

Example 6

Hydrogen passivated Si(100)–2×1 surfaces are prepared by first degassing the sample at 650° C. for at least 6 h and degassing a hydrogen cracking filament at 1600° C. for 10 min. The sample is then flashed repeatedly at 1250° C. After the final flash, the sample is heated to 375° C., and the cracking filament is heated to 1450° C., while the surface is exposed to $2\times10^{-6}$ Torr of hydrogen for 10 min. STM lithography of the Si(100)–2×1:H surface can be performed in two regimes as described in the literature. If the tunneling electrons have energies greater than the separation in energy between the bonding and anti-bonding state of the Si—H bond, patterns may be written in a direct desorption regime. However, the best STM lithographic resolution is obtained on the Si(100)–2×1:H surface when tunneling electrons have insufficient energy to directly desorb the hydrogen. In this lower energy regime, hydrogen may be desorbed through a vibrational heating mechanism. A depassivated square written in this way, at 8.2 K, is shown in FIG. 15C.

Example 7

With FCL, the STM control electronics monitor the tunneling current during patterning. By adjusting threshold parameters for detecting changes in the tunneling current, patterning in the vibrational heating regime may be halted at the precise moment that a desorption event occurs. In this way, the resolution of STM lithography is extended to individual desorption events. Atomic resolution FCL is demonstrated in FIG. 16, where a 3×3 grid of dangling bond sites is written on the Si(100)–2×1:H surface.

Example 8

The STM can also be used for STS studies of individual molecules on silicon surfaces at cryogenic temperatures. In FIG. 17, an example of differential tunneling conductance mapping is shown at 80 K for cyclopentene molecules adsorbed on Si(100). In this experiment, an ac dither bias (amplitude=10 $mV_{rms}$, frequency=3.5 kHz) is superimposed on the dc sample bias. The resulting amplitude of the ac tunneling current response at the driving frequency is detected with a lock-in amplifier and concurrently recorded during the constant current STM image. Differential tunneling conductance maps of this type provide a qualitative map of the local density of states on the surface. FIG. 17A contains a constant current STM image of a submonolayer coverage of cyclopentene on the Si(100) surface, while FIG. 17B shows a representative differential tunneling conductance map of a region of that surface. Under these conditions, the cyclopentene molecules exhibit lower differential tunneling conductance compared to the background silicon surface. Differential tunneling conductance measurements of this type provide additional information regarding the electronic structure of individual molecules mounted on silicon surfaces.

Example 9

Negative differential resistance in individual organic molecules adsorbed on the Si(100) was recently observed at 300 K using this invention. The patterning of styrene-based molecular wires on Si(100) surfaces can also be investigated. By connecting the load lock of a room temperature UHV STM system to a controlled atmosphere glovebox, STM lithography experiments on hydrogen passivated silicon surfaces can extend to the liquid phase. Through the use of the cryogenic variable temperature UHV STM system presented here, these studies can be extended to cryogenic temperatures, as demonstrated in the following examples.

Example 10

The work described in examples 10-14 was performed with the aforementioned cryogenic variable-temperature UHV STM, which is capable of cooling the STM and the sample down to 8.2 K. The STM and sample preparation station are housed in a UHV chamber that maintains a base pressure of $6\times10^{-11}$ torr (1 torr=133 Pa). Degenerately doped p-type (resistivity <0.005 K cm, borondoped) Si(100) was used for all experiments (Virginia Semiconductor, Fredericksburg, Va.). STM imaging and current-voltage measurements used commercially available Pt—Ir probes (Materials Analytic Services, Raleigh, N.C.). Cyclopentene molecules were commercially purchased (Sigma-Aldrich) and loaded into a custom quartz vial that is mounted to a stainless steel gas manifold on the UHV chamber. The cyclopentene molecules exist in the liquid phase at room temperature with a measured vapor pressure of ≈1 torr.

Example 11

The silicon sample is degreased with isopropyl alcohol and dried with nitrogen before being introduced into UHV. The samples are then degassed at ≈600° C. for at least 8 h in an effort to desorb residual hydrocarbons and other volatile contaminants. After the degassing, the sample is flashed twice at ≈1,250° C. for 30 sec, resulting in an atomically pristine 2×1 reconstructed surface. Additional thermal treatment is avoided because boron segregation will occur on the clean Si(100) surface after repeated thermal cycling. At this point, the sample is transferred to the STM for room-temperature verification of the surface quality.

Example 12

Figures 8A, 8B:
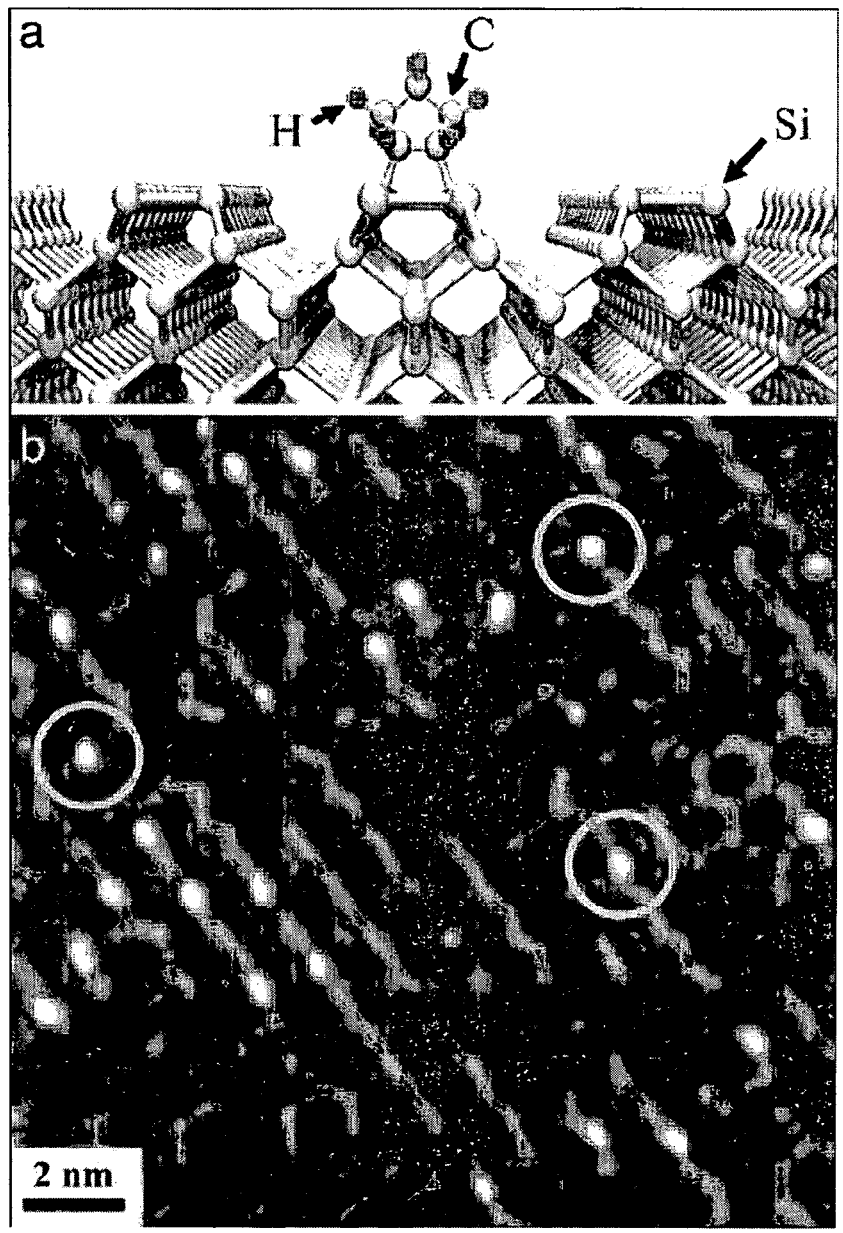
FIGS. 8A-B. Cyclopentene molecules on the Si(100)–2×1 surface. (A) Ball and stick model of cyclopentene bound to the Si(100)–2×1 surface. (B) UHV STM image of isolated cyclopentene molecules on the Si(100)–2×1 surface at a temperature of 80 K. Three of the molecules have been circled.

Before dosing, the cyclopentene undergoes a series of freeze-pump-thaw cycles to remove any residual gases and contaminants from the vial. By using a precision leak valve, the chamber is then backfilled with cyclopentene to a pressure of $10^{-8}$ torr for 90 sec. These dosing conditions lead to a reproducible submonolayer coverage of cyclopentene, as confirmed with room-temperature STM imaging. With minimal delay, the microscope and sample are subsequently cooled with liquid nitrogen. FIG. 8B is a typical STM image of the resulting surface at 80 K. The cyclopentene molecules appear as protrusions centered on the silicon dimer rows with an apparent height of ≈1 Å under the constant current tunneling conditions of 0.1 nA tunneling current and −2 V sample bias. A few of these molecules have been circled in FIG. 8B, for point of reference.

Example 13

STM current-voltage curves are generated by using the following procedure. An STM image is initially taken to identify the location of individual cyclopentene molecules on the silicon surface. Positions for current-voltage measurements are then determined (either over an isolated molecule or over the clean silicon surface) and an additional image is initiated. During this imaging, the tip is scanned in constant-current mode according to the tunneling setpoint conditions (0.1-nA tunneling current and −2-V sample bias) until it reaches the indicated point(s) for taking current-voltage measurements. At these predetermined points, the feedback loop is disabled such that the tip position is held constant, and the sample bias is varied while the tunneling current is recorded. For variable tip-sample spacing measurements, the tip is first moved normal to the sample surface and then held fixed during the current-voltage measurement. After the current-voltage measurement is complete, the STM resumes scanning under constant-current conditions. Consequently, an STM image is concurrently generated that confirms that the initial locations of the molecules are unchanged throughout the measurement.

Example 14

Figures 9A, 9B:
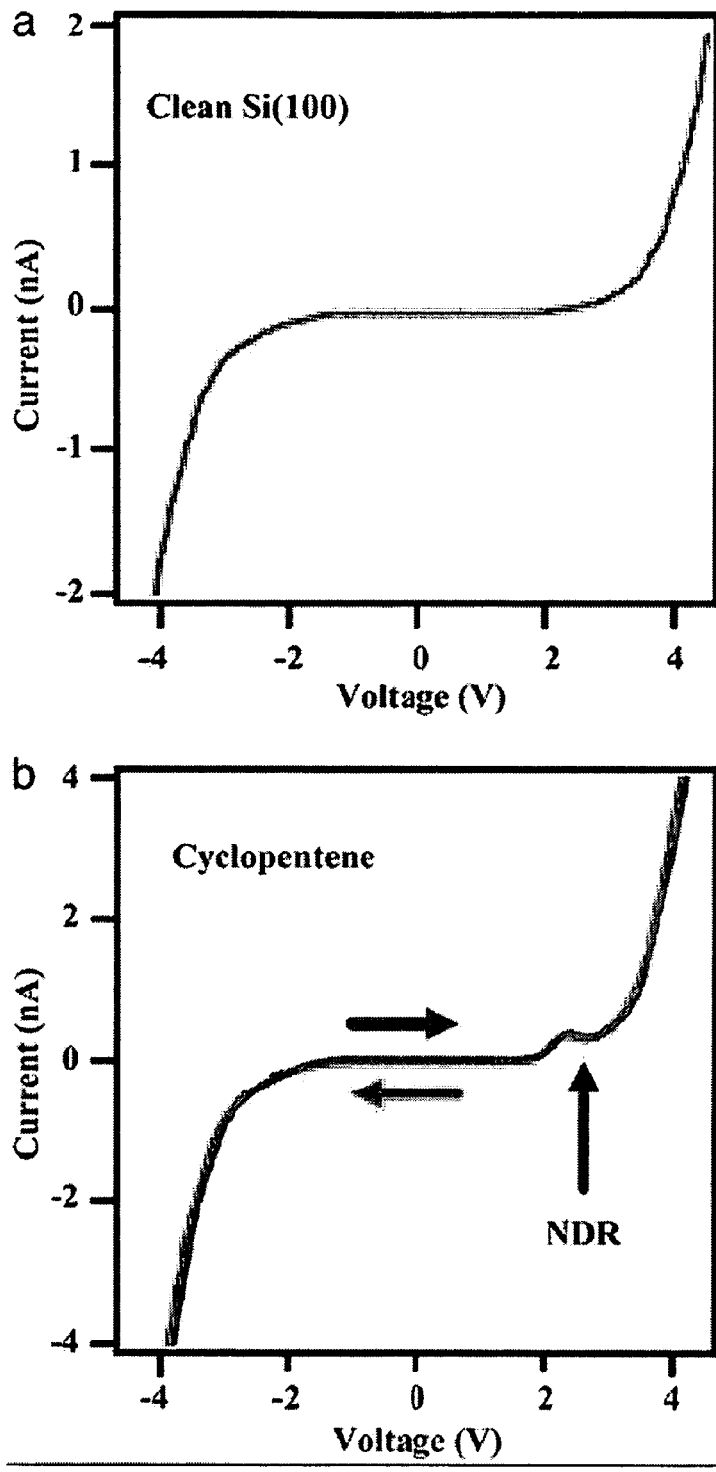
FIGS. 9A-B. Current-voltage measurements taken with an STM apparatus at 80 K. (A) A representative current-voltage curve taken on the clean Si(100)–2×1 surface. (B) A series of four consecutive current-voltage measurements taken over an isolated cyclopentene molecule. The voltage sweep direction alternated between negative to positive and positive to negative. Hysteresis is not observed between the four sweeps, and unipolar NDR is evident at positive bias.

FIG. 9A is a typical current-voltage measurement taken over the clean Si(100)–2×1 surface at 80 K. The current-voltage curve shows no NDR and agrees with expectations for a semiconductor-vacuum-metal tunnel junction. Assuming a one-dimensional tunnel barrier, the tip-sample spacing on the clean Si(100)–2×1 surface is estimated from this current-voltage curve to be ≈10 Å. It should be noted that care was taken not to position the tip over surface-segregated boron dopants, on which NDR was previously reported for the clean Si(100)–2×1 surface. FIG. 9B is a consecutive series of four current-voltage measurements taken over an isolated cyclopentene molecule at 80 K, where the sweep direction of the voltage alternated between each curve. Each of the curves shows clear NDR at positive sample bias, in agreement with previous observations at room temperature. Immediately preceding NDR, a peak is observed in the current-voltage curve, which corresponds with the optimal resonant tunneling condition. The voltage corresponding to this peak in current will be referred to as $V_{peak}$ for the remainder of this paper. In addition, FIG. 9B shows no appreciable hysteresis in these measurements. The lack of hysteresis suggests no stochastic molecular conformational changes as the mechanism for NDR and thus provides further evidence for the resonant tunneling model.

The invention claimed is:

1. A cryogenic variable temperature scanning tunneling microscope apparatus, comprising a scanning tunneling microscope stage component and a cooling system, said cooling system comprising a plurality of interposed compartments, one said compartment between the periphery of another said compartment, said stage component comprising a scanning tunneling microscope scanner and positioned within one of said compartments.

2. The apparatus of claim 1 wherein said cooling system comprises an inner compartment and an outer compartment, said stage component adjustably suspended from said inner compartment.

3. The apparatus of claim 2 comprising a plurality of vibrationally-isolating suspension springs.

4. The apparatus of claim 3 wherein said stage component is coupled to each of said suspension springs with an electrically-insulating mounting component.

5. The apparatus of claim 2 wherein said inner compartment comprises a plurality of support components to position said stage component.

6. The apparatus of claim 1 wherein said scanner comprises a sample holder component comprising a pair of sample holder rails, each said rail comprising a substantially rounded cross-sectional configuration.

7. The apparatus of claim 6 wherein said rails comprise titanium nitride.

8. The apparatus of claim 6 wherein each said rail comprises beryllium copper and titanium nitride thereon.

9. The apparatus of claim 2 wherein a surface of each said compartment defines a plurality of apertures for connector and instrumentation feedthroughs.

10. The apparatus of claim 9 wherein each aperture is configured with a electrically-insulating and heat-sinking component.

11. The apparatus of claim 9 comprising a plurality of heater components on an inside surface of at least one of said compartments.

12. The apparatus of claim 2 wherein each said compartment comprises a re-sealable opening and an optically transparent window therethrough.

13. The apparatus of claim 1 wherein said cooling system is within a vacuum chamber component.

14. The apparatus of claim 2 wherein said stage component comprises a mirror, for visual access to a scanner tip-sample interface.

15. A cryogenic variable temperature scanning tunneling microscope apparatus, comprising a scanning tunneling microscope stage component and a cooling system, said cooling system comprising a plurality of interposed inner and outer compartments, one said compartment between the periphery of another said compartment, said stage component comprising a scanning tunneling microscope concentric piezoelectric scanner and positioned within one of said compartments, said cooling system and said stage component within a vacuum chamber component.

16. The apparatus of claim 15 wherein said stage component is adjustably suspended from said inner compartment, each said compartment defining at least one dosing aperture, for at least one of sample access and apparatus manipulation.

17. The apparatus of claim 16 comprising a plurality of vibrationally-isolating suspension springs.

18. The apparatus of claim 17 wherein said stage component is coupled to each of said suspension springs with an electrically-insulating mounting component, said stage component comprising at least one eddy current damping neodymium magnet coupled thereto.

19. The apparatus of claim 15 wherein said stage component comprises a sample holder component coupled to said piezoelectric scanner, said holder component comprising a pair of sample holder rails, each said rail comprising a substantially rounded cross-sectional configuration.

20. The apparatus of claim 19 wherein said rails comprise titanium nitride coated beryllium copper.

21. The apparatus of claim 15 wherein a surface of each said compartment defines a plurality of apertures for connector and instrumentation feedthroughs.

22. The apparatus of claim 21 comprising a plurality of heater components on an inside surface of at least one of said compartments.

23. The apparatus of claim 15 wherein each compartment comprises at least one re-sealable opening and a sapphire viewport.

24. The apparatus of claim 23 wherein said vacuum chamber component comprises a plurality of viewports and wobblestick apertures.

25. A method of using a cryogenic variable temperature vacuum scanning tunneling microscope apparatus to quantitatively estimate molecular orbital energies of a single molecule, said method comprising:
   providing a substrate degeneratively p-type doped with a molecular component, as a sample in a cryogenic scanning tunneling microscope apparatus, said apparatus comprising a piezoelectric scanner tip;
   applying a positive bias across said sample, said bias inducing an increase in conduction; and
   obtaining a multiplicity of current-voltage measurements as a function of distance between said tip and said molecular component, said measurements obtained at a temperature sufficient to maintain a substantially constant tip-sample distance over said measurements, said bias sufficient to induce resonance with the highest occupied molecular orbital of said molecular component.

26. The method of claim 25 wherein said bias is increased sufficient to reduce conduction.

27. The method of claim 25 wherein said substrate comprises an electrically-insulating material.

28. The method of claim 27 wherein said substrate comprises silicon.

29. The method of claim 25 wherein said molecular component comprises a cyclopentene moiety.

30. The method of claim 25 wherein said temperature is about 80 K.

* * * * *

UNITED STATES PATENT AND TRADEMARK OFFICE
CERTIFICATE OF CORRECTION

PATENT NO.         : 7,414,250 B1
APPLICATION NO. : 11/291210
DATED              : August 19, 2008
INVENTOR(S)        : Mark C. Hersam and Edward T. Foley It is certified that error appears in the above-identified patent and that said Letters Patent is hereby corrected as shown below:

Col. 16, Line 50 "<0.005 K cm" should be -- <0.005 $\Omega$ cm --

Signed and Sealed this

Twentieth Day of January, 2009

JON W. DUDAS
*Director of the United States Patent and Trademark Office*